（12) United States Patent
Bigot et al.

(10) Patent No.: US 7,348,434 B2
(45) Date of Patent: Mar. 25, 2008

(54) 4-SUBSTITUTED QUINOLINE DERIVATIVES, METHOD AND INTERMEDIATES FOR THEIR PREPARATION AND PHARMACEUTICAL COMPOSITIONS CONTAINING THEM

(76) Inventors: Antony Bigot, 8, rue Jean Rostand, F-91300 Massy (FR); Serge Mignani, 14, Avenue de Robinson, F-92290 Chatenany Malabry (FR); Baptiste Ronan, 15, allée des Noisetiers, F-92140 Clamart (FR); Michel Tabart, 3, Rue Paul Langevin, F-91290 La Norville (FR); Fabrice Viviani, 46, rue Jules Fossier, F-95380 Louvres (FR)

( * ) Notice: Subject to any disclaimer, the term of this patent is extended or adjusted under 35 U.S.C. 154(b) by 451 days.

(21) Appl. No.: 10/913,222

(22) Filed: Aug. 6, 2004

(65) Prior Publication Data
US 2005/0032800 A1  Feb. 10, 2005

Related U.S. Application Data

(60) Provisional application No. 60/517,433, filed on Nov. 5, 2003.

(30) Foreign Application Priority Data
Aug. 8, 2003 (FR) ................... 03 09754

(51) Int. Cl.
C07D 215/38 (2006.01)
(52) U.S. Cl. .................................... 546/157
(58) Field of Classification Search ............... 546/157
See application file for complete search history.

(56) References Cited

U.S. PATENT DOCUMENTS

| 3,714,168 A | | 1/1973 | Olsen | |
|---|---|---|---|---|
| 4,002,757 A | * | 1/1977 | Cale, Jr. | .................. 514/314 |
| 4,039,678 A | * | 8/1977 | Cale, Jr. | .................. 514/426 |

FOREIGN PATENT DOCUMENTS

| EP | 0031753 | 7/1981 |
|---|---|---|
| EP | 0042781 | 12/1981 |
| EP | 0291172 | 11/1988 |
| FR | 2394292 | 1/1979 |
| GB | 240051 | 9/1925 |
| JP | 04 024782 | 1/1992 |
| WO | WO 98/46572 | 10/1998 |
| WO | WO 99/37635 | 7/1999 |
| WO | WO 00/21948 | 4/2000 |
| WO | WO 01/07433 | 2/2001 |
| WO | WO 02/08224 | 1/2002 |
| WO | WO 03/064421 | 8/2003 |

OTHER PUBLICATIONS

O. E. Schultz et al., Synthese Von 1-(4-Chinolyl)-2-Alkylamino-Athanolen, Arch. Phasmaz, (1972, pp. 244-248, vol. 305, No. 4).
Saggiomo et al., Antimalarial Potency of 2-Benzoyl-4-quinolinemethanols, Journal of Medical Chemistry, vol. 15, No. 9, 1972, pp. 989-994.

* cited by examiner

*Primary Examiner*—D. Margaret Seaman
(74) *Attorney, Agent, or Firm*—Harness, Dickey & Pierce, P.L.C.

(57) ABSTRACT

The invention relates to 4-substituted quinoline derivatives of general formula:

(I)

which are active as antimicrobials, in which:
$X_1$, $X_2$, $X_3$, $X_4$ and $X_5$ represent $>C-R'_1$ to $>C-R'_5$ respectively, or alternatively at most one represents nitrogen,
Y represents CHR, CO, CROH, $CRNH_2$, CRF or $CF_2$, R being a hydrogen or alkyl, m is 0, 1 or 2 and n is 0 or 1, $R_2$ represents a radical R, $-CO_2R$, $-CH_2CO_2R$, $-CH_2-CH_2CO_2R$, $-CONH_2$, $-CH_2-CONH_2$, $-CH_2-CH_2-CONH_2$, $-CH_2OH$, $-CH_2-CH_2OH$, $-CH_2-NH_2$, $-CH_2-CH_2-NH_2$ or $-CH_2-CH_2-CH_2-NH_2$, R being as defined above,
$R_3$ represents phenyl, heteroaryl or alk-$R°_3$, where alk is alkyl and $R°_3$ represents various groups, where appropriate containing oxygen, sulfur or amine, in their enantiomeric or diastereoisomeric forms or their mixtures, and/or where appropriate in the syn or anti form or their mixtures, and their salts.

17 Claims, No Drawings

4-SUBSTITUTED QUINOLINE DERIVATIVES, METHOD AND INTERMEDIATES FOR THEIR PREPARATION AND PHARMACEUTICAL COMPOSITIONS CONTAINING THEM

This application claims the benefit of U.S. Provisional Application No. 60/517,433, filed Nov. 5, 2003 and benefit of priority of French Patent Application No. 03/09,754, filed Aug. 8, 2003, both of which are incorporated herein by reference in their entirety.

BACKGROUND OF THE INVENTION

1. Field of the Invention

The present invention relates to 4-substituted quinoline derivatives of general formula (I):

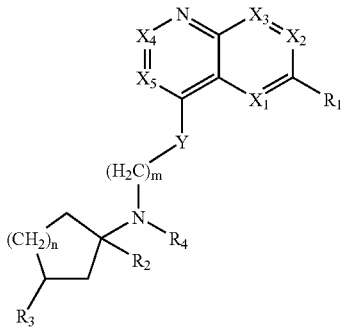

which are active as antimicrobials. The invention also relates to the method and intermediates for their preparation and the pharmaceutical compositions containing them.

2. Description of the Art

In patent applications WO 99/37635 and WO 00/43383 there are described antimicrobial quinolylpropylpiperidine derivatives of general formula:

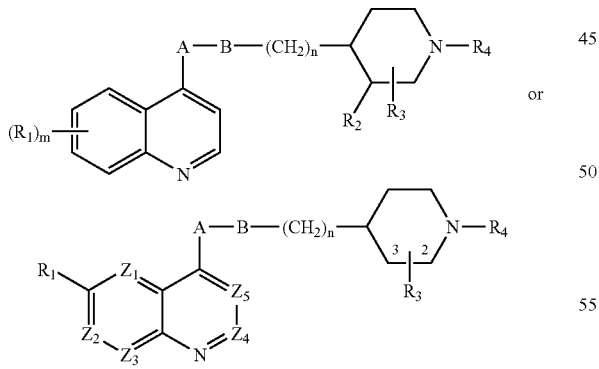

in which the radical $R_1$ is in particular alkoxy (C1-6), $R_2$ is hydrogen, $R_3$ is at the 2 or 3 position and represents alkyl (C1-6) which may be optionally substituted with 1 to 3 substituents chosen from thiol, halogen, alkylthio, trifluoromethyl, carboxy, alkyloxycarbonyl, alkylcarbonyl, alkenyloxycarbonyl, alkenylcarbonyl, hydroxyl optionally substituted with alkyl, $R_4$ is a group —$CH_2$—$R_5$ for which $R_5$ is selected from alkyl, hydroxyalkyl, alkenyl, alkynyl, tetrahydrofuryl, optionally substituted phenylalkyl, optionally substituted phenylalkenyl, optionally substituted heteroarylalkyl, optionally substituted heteroaroyl . . . , n is 0 to 2, m is 1 or 2 and A and B are in particular oxygen, sulfur, sulfinyl, sulfonyl, $NR_{11}$, $CR_6R_7$ for which $R_6$ and $R_7$ represent H, thiol, alkylthio, halo, trifluoromethyl, alkenyl, alkenylcarbonyl, hydroxyl, amino, and $Z_1$ to $Z_5$ are N or $CR_{1a}$ . . . .

Other applications, in particular WO 00/21952, WO 00/21948, WO 01/07432, WO 01/07433, WO 03/010138, or alternatively WO 02/40474 or WO 02/072572 describe other 4-(quinolylpropyl)piperidine derivatives, substituted in particular at the 3 position or disubstituted at the 4 position, which are active in the same field. European application EP 30044 moreover describes related derivatives which are active in the cardiovascular field.

All of the references described herein are incorporated herein by reference in their entirety.

SUMMARY OF THE INVENTION

It has now been found, and that is what constitutes the subject of the present invention, that the compounds of general formula (I) in which:

$X_1$, $X_2$, $X_3$, $X_4$ and $X_5$ represent >C—$R'_1$ to >C—$R'_5$ respectively, or alternatively at most one of them represents a nitrogen atom, $R_1$, $R'_1$, $R'_2$, $R'_3$, $R'_4$ and $R'_5$ are identical or different and represent a hydrogen or halogen atom or an alkyl, cycloalkyl, phenyl, phenylthio, mono- or bicyclic heteroaryl or heteroarylthio, OH, SH, alkyloxy, difluoromethoxy, trifluoromethoxy, alkylthio, trifluoromethylthio, cycloalkyloxy, cycloalkylthio, acyl, acyloxy, acylthio, cyano, carboxyl, alkyloxycarbonyl, cycloalkyloxycarbonyl, nitro, —NRaRb or —CONRaRb radical (for which Ra and Rb can represent hydrogen, alkyl, cycloalkyl, phenyl, mono- or bicyclic heteroaryl or Ra and Rb form together with the nitrogen atom to which they are attached a 5- or 6-membered heterocycle which may optionally contain another heteroatom chosen from O, S or N and carrying, where appropriate, an alkyl, phenyl or mono- or bicyclic heteroaryl substituent on the nitrogen atom or, where appropriate, in which the sulfur atom is oxidized to the sulfinyl or sulfonyl state), or represent a methylene radical substituted with fluoro, hydroxyl, alkyloxy, alkylthio, cycloalkyloxy, cycloalkylthio, phenyl, mono- or bicyclic heteroaryl, carboxyl, alkyloxycarbonyl, cycloalkyloxycarbonyl, —NRaRb or —CONRaRb for which Ra and Rb are as defined above, or represent phenoxy, heterocyclyloxy, benzyloxy, heterocyclylmethyloxy, or alternatively $R_1$ may also represent difluoromethoxy, or a radical having the structure —$C_mF_{2m'+1}$, —$SC_mF_{2m'+1}$ or —$OC_mF_{2m'+1}$ for which m' is an integer from 1 to 6 or alternatively $R'_5$ may also represent trifluoroacetyl, m is equal to 0, 1 or 2;

n is equal to 0 or 1;

Y represents a group CHR, C=O or, when m is equal to 1 or 2, CROH, $CRNH_2$, CRF or $CF_2$, R being a hydrogen atom or an alkyl ($C_{1-6}$) radical;

$R_2$ represents a radical R, —$CO_2R$, —$CH_2CO_2R$, —$CH_2$—$CH_2CO_2R$, —$CONH_2$, —$CH_2$—$CONH_2$, —$CH_2$—$CH_2$—$CONH_2$, —$CH_2OH$, —$CH_2$—$CH_2OH$, —$CH_2$—$NH_2$—$CH_2$—$CH_2$—$NH_2$ or —$CH_2$—$CH_2$—$CH_2$—$NH_2$, R being as defined above;

R₃ represents a radical phenyl, mono- or bicyclic heteroaryl, alk-R°₃ for which alk is an alkylene radical and R°₃ represents hydrogen, halogen, hydroxyl, alkyloxy, alkylthio, alkylsulfinyl, alkylsulfonyl, alkylamino, dialkylamino, cycloalkyl, cycloalkyloxy, cycloalkylthio, cycloalkylsulfinyl, cycloalkylsulfonyl, cycloalkylamino, N-cycloalkyl-N-alkylamino, —N-(cycloalkyl)₂, acyl, cycloalkylcarbonyl, phenyl, phenoxy, phenylthio, phenylsulfinyl, phenylsulfonyl, phenylamino, N-alkyl-N-phenylamino, N-cycloalkyl-N-phenylamino, —N-(phenyl)₂, phenylalkyloxy, phenylalkylthio, phenylalkylsulfinyl, phenylalkylsulfonyl, phenylalkylamino, N-alkyl-N-phenylaminoalkyl, N-cycloalkyl-N-phenylalkylamino, benzoyl, mono- or bicyclic heteroaryl, heteroaryloxy, heteroarylthio, heteroarylsulfinyl, heteroarylsulfonyl, heteroarylamino, N-alkyl-N-heteroarylamino, N-cycloalkyl-N-heteroarylamino, heteroarylcarbonyl, heteroarylalkyloxy, heteroarylalkylthio, heteroarylalkylsulfinyl, heteroarylalkylsulfonyl, heteroarylalkylamino, N-alkyl-N-heteroarylaminoalkyl, N-cycloalkyl-N-heteroarylaminoalkyl, (the heteroaryl parts mentioned above being mono- or bicyclic), carboxyl, alkyloxycarbonyl, —NRaRb or —CO—NRaRb for which Ra and Rb respectively represent hydrogen, alkyl, cycloalkyl, phenyl, mono- or bicyclic heteroaryl, or one of Ra or Rb represents hydroxyl, alkyloxy, cycloalkyloxy, or Ra and Rb form together with the nitrogen atom to which they are attached a 5- or 6-membered heterocycle which may optionally contain another heteroatom chosen from O, S and N and carrying, where appropriate, an alkyl, phenyl or mono- or bicyclic heteroaryl substituent on the nitrogen atom or where appropriate in which the sulfur atom is oxidized to the sulfinyl or sulfonyl state, or alternatively R°₃ represents —CR'b=CR'c-R'a for which R'a represents phenyl, phenylalkyl, heteroaryl or heteroarylalkyl in which the heteroaryl part is mono- or bicyclic, phenoxyalkyl, phenylthioalkyl, phenylsulfinylalkyl, phenylsulfonylalkyl, phenylaminoalkyl, N-alkyl-N-phenylaminoalkyl, heteroaryloxyalkyl, heteroarylthioalkyl, heteroarylsulfinylalkyl, heteroarylsulfonylalkyl, heteroarylaminoalkyl, N-alkyl-N-heteroarylaminoalkyl, heteroarylthio, heteroarylsulfinyl, heteroarylsulfonyl, (the heteroaryl parts mentioned above being mono- or bicyclic), phenylthio, phenylsulfinyl, phenylsulfonyl, and for which R'b and R'c represent hydrogen, alkyl or cycloalkyl, or alternatively R°₃ represents a radical —C≡C—Rd for which Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, heteroarylaminoalkyl, N-alkyl-N-heteroarylaminoalkyl, (the heteroaryl parts mentioned above being mono- or bicyclic aromatic), or alternatively R°₃ represents a radical —CF₂-phenyl or mono- or bicyclic —CF₂-heteroaryl, it being understood that the phenyl, benzyl, benzoyl or heteroaryl radicals or portions mentioned above are optionally substituted on the ring with 1 to 4 substituents chosen from halogen, hydroxyl, alkyl, alkyloxy, alkyloxyalkyl, haloalkyl, trifluoromethyl, trifluoromethoxy, trifluoromethylthio, carboxyl, alkyloxycarbonyl, cyano, alkylamino, —NRaRb for which Ra and Rb are as defined above, phenyl, hydroxyalkyl, alkylthioalkyl, alkylsulfinylalkyl, alkylsulfonylalkyl; R₄ represents a radical R, —CHO, —COCH₃, —CH₂CO₂H or —COCH₂NH₂;

it being understood that the alkyl or acyl radicals and portions contain (unless specifically stated) 1 to 10 carbon atoms in the form of a straight or branched chain and that the cycloalkyl radicals contain 3 to 6 carbon atoms, in their enantiomeric or diastereoisomeric forms or mixtures of these forms, and/or where appropriate in syn or anti form or mixtures thereof, and their salts, are very potent antibacterial agents.

DETAILED DESCRIPTION OF THE INVENTION

It is understood that when the radicals represent or carry a halogen atom, the halogen is chosen from fluorine, chlorine, bromine or iodine, and is preferably fluorine.

In the above general formula, when the radicals represent or carry a mono- or bicyclic heteroaryl substituent, the latter contains 5 to 10 members and may be chosen (without limitation) from thienyl, furyl, pyrrolyl, imidazolyl, thiazolyl, oxazolyl, thiadiazolyl, oxadiazolyl, tetrazolyl, pyridyl, pyridazinyl, pyrazinyl, pyrimidinyl, indolyl, benzothienyl, benzofuranyl, indazolyl, benzothiazolyl, naphthyridinyl, quinolyl, isoquinolyl, cinnolyl, quinazolyl, quinoxalyl, benzoxazolyl, benzimidazolyl which may be optionally substituted with the substituents mentioned above.

Among the compounds of general formula (I), there may be mentioned in particular those in which $X_1$, $X_2$, $X_3$, $X_4$ and $X_5$ are as defined above, $R_1$, $R'_1$, $R'_2$, $R'_3$, $R'_4$ and $R'_5$ are identical or different and represent a hydrogen or halogen atom or an alkyl or alkyloxy radical, or represent a methylene radical substituted with alkyloxy:

m is equal to 1;

n is equal to 1;

Y represents a radical $CH_2$, CHOH, CHF, $CHNH_2$ or C=O;

$R_2$ is as defined above, and $R_3$ represents a radical alk-$R°_3$ for which alk is an alkylene radical and $R°_3$ represents alkyloxy, alkylthio, alkylamino, dialkylamino, cycloalkyloxy, cycloalkylthio, cycloalkylamino, N-cycloalkyl-N-alkylamino, —N-(cycloalkyl)₂, phenoxy, phenylthio, phenylamino, N-alkyl-N-phenylamino, N-cycloalkyl-N-phenylamino, phenylalkyloxy, phenylalkylthio, phenylalkylamino, N-alkyl-N-phenylaminoalkyl, N-cycloalkyl-N-phenylalkylamino, heteroaryl, oxy, heteroarylthio, heteroarylamino, N-alkyl-N-heterocyclylamino, N-cycloalkyl-N-heteroarylamino, heteroarylcarbonyl, heteroarylalkyloxy, heteroarylalkylthio, heteroarylalkylamino, N-alkyl-N-heteroarylaminoalkyl, N-cycloalkyl-N-heteroarylaminoalkyl, (the heteroaryl parts cited above being mono- or bicyclic), —NRaRb or —CO—NRaRb for which Ra and Rb are as defined above, or alternatively R°₃ represents —CR'b=CR'c-R'a for which R'a represents phenyl, phenylalkyl, heteroaryl or heteroarylalkyl, phenoxyalkyl, phenylthioalkyl, phenylaminoalkyl, N-alkyl-N-phenylaminoalkyl, heteroaryloxyalkyl, heteroarylthioalkyl, heteroarylaminoalkyl, N-alkyl-N-heteroarylaminoalkyl, heteroarylthio, (the heteroaryl parts cited above being mono- or bicyclic), or phenylthio, and for which R'b and R'c represent hydrogen, alkyl or cycloalkyl, or alternatively R°₃ represents a radical —C≡C—Rd for which Rd is alkyl, phenyl, phenylalkyl, phenoxyalkyl, phenylthioalkyl, N-alkyl-N-phenylaminoalkyl, heteroaryl, heteroarylalkyl, heteroaryloxyalkyl, heteroarylthioalkyl, heteroarylaminoalkyl, N-alkyl-N-heteroarylaminoalkyl, (the heteroaryl parts cited above being mono- or bicyclic), or alternatively $R°_3$ represents a —$CF_2$-phenyl or mono- or bicyclic —$CF_2$-heteroaryl radical;

$R_4$ is as defined above;

it being understood that the phenyl, benzyl, benzoyl or heteroaryl radicals or portions mentioned above may be optionally substituted as envisaged above, in their enantiomeric or diastereoisomeric forms or mixtures of these forms, and/or where appropriate in syn or anti form or mixtures thereof, and their salts, and more particularly those in which $X_1$, $X_2$, $X_3$, $X_4$ and $X_5$ represent >C—$R'_1$ to >C—$R'_5$ respectively, $R_1$, $R'_1$, $R'_2$, $R'_3$, $R'_4$, $R'_5$ are identical or different and represent a hydrogen or halogen atom or an alkyl or alkyloxy radical, or represent a methylene radical substituted with alkyloxy;

m is equal to 1;

n is equal to 1;

Y represents a radical $CH_2$, CHOH, CHF, $CHNH_2$ or C=O;

$R_2$ is as defined above, and $R_3$ represents a radical alk-$R°_3$ for which alk is an alkylene radical and $R°_3$ represents cycloalkyloxy, cycloalkylthio, phenoxy, phenylthio, phenylalkyloxy, phenylalkylthio, heteroaryl, oxy, heteroarylthio, heteroarylalkyloxy, heteroarylalkylthio, (the heteroaryl parts cited above being mono- or bicyclic) or alternatively $R_3$ represents —CR'b=CR'c-R'a for which R'a represents phenyl, phenylalkyl, heteroaryl, heteroarylalkyl, phenoxyalkyl, phenylthioalkyl, heteroaryloxyalkyl, heteroarylthioalkyl, heteroarylthio (the heteroaryl parts cited above being mono- or bicyclic), or phenylthio, and for which R'b and R'c represent hydrogen, alkyl or cycloalkyl, or alternatively $R°_3$ represents a radical —C≡C—Rd for which Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, (the heteroaryl parts cited above being mono- or bicyclic);

$R_4$ represents a radical R;

it being understood that the phenyl, benzyl, benzoyl or heteroaryl radicals or portions mentioned above may be optionally substituted as envisaged above, in their enantiomeric or diastereoisomeric forms or mixtures of these forms, and/or where appropriate in syn or anti form or mixtures thereof, and their salts.

Among the compounds of general formula (I), the subject of the invention is most particularly any one of those whose names follow:

1-[(E)-3-(2,5-difluorophenyl)allyl]-3-[2-(3-fluoro-6-methoxy-4-quinolinyl)ethylamino]-3-pyrrolidinecarboxylic acid;

1-[(E)-3-(2,5-difluorophenyl)allyl]-3-[2-(6-methoxy-4-quinolinyl)ethylamino]-3-pyrrolidinecarboxylic acid;

methyl 1-[(E)-3-(2,5-difluorophenyl)allyl]-3-[2-(3-fluoro-6-methoxy-4-quinolinyl)ethylamino]-3-pyrrolidinecarboxylate;

methyl 1-[(E)-3-(2,5-difluorophenyl)allyl]-3-[2-(6-methoxy-4-quinolinyl)ethylamino]pyrrolidinecarboxylate;

methyl 1-[(E)-3-(2,5-difluorophenyl)allyl]-3-[2-(3-chloro-6-methoxy-4-quinolinyl)ethylamino]pyrrolidinecarboxylate;

methyl 1-[(E)-3-(2,5-difluorophenyl)allyl]-3-[2-(3-chloro-6-methoxy-4-quinolinyl)ethylamino]-3-pyrrolidinecarboxylate;

in their enantiomeric or diastereoisomeric forms or mixtures of these forms, and/or where appropriate in syn or anti form or mixtures thereof, and their salts.

Among the compounds of general formula (I), there may also be mentioned those whose names follow:

1-[(2E)-3-(2,5-difluorophenyl)-2-propenyl]-3-[[2-(3-fluoro-6-methoxy-4-quinolinyl)ethyl]methylamino]-3-pyrrolidinecarboxylic acid;

1-[(2E)-3-(2,5-difluorophenyl)-2-propenyl]-3-[[2-(3-fluoro-6-methoxy-4-quinolinyl)ethyl]formylamino]-3-pyrrolidinecarboxylic acid;

3-[(aminoacetyl)[2-(3-fluoro-6-methoxy-4-quinolinyl)ethyl]amino]-1-[(2E)-3-(2,5-difluorophenyl)-2-propenyl]-3-pyrrolidinecarboxylic acid;

3-[(carboxymethyl)[2-(3-fluoro-6-methoxy-4-quinolinyl)ethyl]amino]-1-[(2E)-3-(2,5-difluorophenyl)-2-propenyl]-3-pyrrolidinecarboxylic acid;

N-[1-[(2E)-3-(2,5-difluorophenyl)-2-propenyl]-3-pyrrolidinyl]-3-fluoro-6-methoxy-4-quinolineethanamine;

N-[1-[(2E)-3-(2,5-difluorophenyl)-2-propenyl]-3-pyrrolidinyl]-N-[2-(3-fluoro-6-methoxy-4-quinolinyl)-ethyl]glycine;

N-[1-[(2E)-3-(2,5-difluorophenyl)-2-propenyl]-3-pyrrolidinyl]-3-fluoro-6-methoxy-N-methyl-4-quinolineethanamine;

1-[(2E)-3-(2,5-difluorophenyl)-2-propenyl]-3-[[2-(3-fluoro-6-methoxy-4-quinolinyl)ethyl]amino]-3-pyrrolidinemethanol;

1-[(2E)-3-(2,5-difluorophenyl)-2-propenyl]-3-[[2-(3-fluoro-6-methoxy-4-quinolinyl)ethyl]amino]-3-pyrrolidinecarboxamide;

N-[3-(aminomethyl)-1-[(2E)-3-(2,5-difluorophenyl)-2-propenyl]-3-pyrrolidinyl]-3-fluoro-6-methoxy-4-quinolineethanamine;

α-[[[1-[(2E)-3-(2,5-difluorophenyl)-2-propenyl]-3-pyrrolidinyl]amino]methyl]-3-fluoro-6-methoxy-4-quinolinemethanol;

in their enantiomeric or diastereoisomeric forms or mixtures of these forms, and/or where appropriate in the syn or anti form or mixtures thereof, and their salts.

According to the invention, the products of general formula (I) may be obtained by condensing the chain $R_3$ with the 4-substituted quinoline derivative of general formula (II):

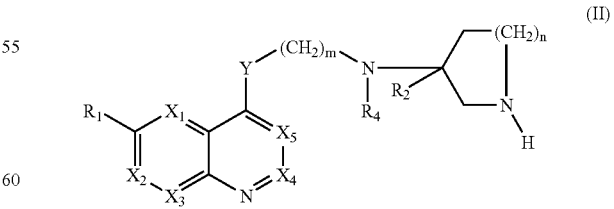

in which $X_1$, $X_2$, $X_3$, $X_4$, $X_5$, $R_1$, $R_2$, Y, m and n are defined as above, $R_2$ and $R_4$ being protected when they carry a carboxyl radical, followed where appropriate by the removal of the group protecting the carboxyl radical, optionally by the separation of the enantiomeric or diastereoisomeric forms and/or where appropriate of the syn or anti forms and optionally by the conversion of the product obtained to a salt.

The condensation of the chain $R_3$ with the heterocyclic nitrogen is advantageously carried out by the action of a derivative of general formula (IIa):

$$R_3—X \qquad (IIa)$$

in which $R_3$ is as defined above and X represents a halogen atom, a methylsulfonyl radical, a trifluoromethylsulfonyl or p-toluenesulfonyl radical, the procedure being carried out in an anhydrous, preferably inert, medium, in an organic solvent such as an amide (dimethylformamide for example), a ketone (acetone for example) or a nitrile (acetonitrile for example) in the presence of a base such as a nitrogenous organic base (for example triethylamine) or an inorganic base (alkali metal carbonate: potassium carbonate for example) at a temperature of between 20° C. and the reflux temperature of the solvent. The nitrogen atom of the pyrrolidine ring of the derivative of general formula (II) is optionally protected according to the customary methods compatible with the remainder of the molecule or the reaction; the protection is performed for example with a protecting radical chosen from benzyl, t-butoxycarbonyl and benzyloxycarbonyl groups, and this nitrogen atom is released prior to the condensation with the derivative of formula (IIa), in particular by acid hydrolysis.

Preferably, a derivative of general formula (IIa) for which X is a chlorine, bromine or iodine atom is caused to act.

Conditions under which it is possible to carry out the condensation between the derivatives of general formulae (II) and (IIa) are also described in application WO 02/40474. When $R_3$ is a radical -alk-$R^o_3$ in which $R^o_3$ is a group —C≡C—Rd, in which Rd is as defined above, an alkynyl halide is intermediately condensed and then the desired radical is condensed with the alkyne thus obtained. When $R_3$ represents a radical -alk-$R^o_3$ for which alk is an alkyl radical and $R^o_3$ represents a phenoxy, phenylthio, phenylamino, heteroaryloxy, heteroarylthio or heteroarylamino radical, it is also possible to construct the chain by first condensing a chain HO-alk-X for which X is a halogen atom, preferably iodine, under the conditions described above for the reaction of the product of general formula (IIa), and then, where appropriate, by converting the hydroxyalkyl chain to a haloalkyl, methanesulfonylalkyl or p-toluenesulfonylalkyl chain and finally by causing an aromatic derivative having the structure $R^o_3H$ or $R^o_3H_2$ to act in a basic medium.

The conversion of the hydroxylated chain to a haloalkyl or p-toluenesulfonyl chain is carried out according to the customary halogenation or sulfonylation methods, in particular a halogenating agent such as thionyl chloride, the halogenated derivatives of phosphorus (phosphorus trichloride or tribromide for example) or a sulfonylating agent such as for example methanesulfonyl chloride, p-toluenesulfonyl chloride or trifluoromethanesulfonic anhydride is caused to act. The reaction is carried out in an organic solvent such as a chlorinated solvent (dichloromethane or chloroform for example), at a temperature of between 0 and 60° C. In some cases, it may be advantageous to carry out the procedure in the presence of a base such as pyridine or triethylamine.

The reaction of the aromatic derivative $R_3H$ or $R_3H_2$ is advantageously carried out as described above for the action of the derivative of general formula (IIa), in an organic solvent such as an amide (dimethylformamide for example), a ketone (acetone for example), a nitrile (acetonitrile for example), in the presence of a base such as a nitrogenous organic base (for example triethylamine) or an inorganic base (alkali metal carbonate: potassium carbonate for example) at a temperature of between 20° C. and the reflux temperature of the reaction mixture. It may be advantageous to carry out the procedure in the presence of potassium iodide. It is also possible to carry out the procedure in an ether (tetrahydrofuran for example) under dehydration conditions in the presence, for example, of diisopropylcarbodiimide and triphenylphosphine.

It is understood that if the radicals $R_3$ carry carboxyl or amino substitutes, the latter are protected beforehand, and then released after the reaction. The procedure is carried out according to methods well known to a person skilled in the art which do not adversely affect the remainder of the molecule, in particular according to the methods described by T. W. Greene and P. G. M. Wuts, Protective Groups in Organic Synthesis (2nd ed.), A. Wiley—Interscience Publication (1991), or by Mc Omie, Protective Groups in Organic Chemistry, Plenum Press (1973).

The protected carboxyl radical carried by $R_2$ or $R_4$ may be chosen from easily hydrolyzable esters. By way of example, there may be mentioned methyl, benzyl or tert-butyl esters, or alternatively phenylpropyl or allyl esters. Optionally, the protection of the carboxyl radical is carried out simultaneously with the reaction.

Where appropriate, the protection of the amino radical is carried out by means of the customary protecting radicals mentioned in the above references.

The introduction and the removal of these protecting radicals are carried out according to methods known to a person skilled in the art. According to the invention, the derivatives of general formula (I) for which $R_2$ is hydroxymethyl or hydroxyethyl may be prepared by the action of an appropriate reducing agent on a derivative for which $R_2$ is carboxyl or carboxymethyl or protected carboxyl or protected carboxymethyl. A ketone functional group which may be present should then be intermediately protected.

Also according to the invention, the products of general formula (I) for which $R_2$ is carboxymethyl or carboxyethyl may also be prepared from the derivatives for which $R_2$ is hydroxymethyl or hydroxyethyl, by the action on the latter of a halogenating or tosylating agent, and then of a cyanating agent and finally hydrolysis of the nitrile.

Also according to the invention, the products of general formula (I) for which $R_2$ is —$CONH_2$, —$CH_2$—$CONH_2$ or —$CH_2$—$CH_2$—$CONH_2$ may be prepared from corresponding acids or esters by amidation with ammonia.

Also according to the invention, the products of general formula (I) for which $R_2$ is —$CH_2$—$NH_2$, —$(CH_2)_2$—$NH_2$ or —$(CH_2)_3$—$NH_2$ may be prepared from corresponding amides by reduction.

It is possible to carry out the reduction of the protected carboxyl according to the customary methods which do not adversely affect the remainder of the molecule, in particular by the action of a hydride (lithium aluminum hydride or diisobutyl aluminum hydride for example) in a solvent such as an ether (tetrahydrofuran for example) at a temperature of between 20 and 60° C. A ketone functional group which may be present is intermediately protected and then deprotected according to conventional methods known to a person skilled in the art, in particular via a cyclic or noncyclic acetal.

The reduction of the free carboxyl may be carried out according to methods which are also known to a person skilled in the art, for example by hydrogenation in the presence of a rhodium- or ruthenium-based catalyst, by the action of sodium borohydride in the presence of a Lewis acid or of lithium aluminum hydride in ether. Preferably, the ketone functional group is in this case also protected in an intermediate phase.

The conversion of the hydroxymethyl or hydroxyethyl radical to a carboxymethyl or carboxyethyl radical is carried out according to the customary methods which do not adversely affect the remainder of the molecule, in particular by the action of a halogenating agent such as for example thionyl chloride or phosphorus trichloride or phosphorus tribromide, or of a tosylating agent, followed by an alkali metal cyanide, for example potassium cyanide or sodium cyanide, in order to prepare the corresponding cyanomethyl derivative, followed by hydrolysis of the nitrile.

The halogenation may be carried out in a chlorinated solvent (dichloromethane or chloroform for example), at a temperature of between 0° C. and the reflux temperature of the solvent.

The amidation reaction with ammonia is carried out under the customary conditions known to persons skilled in the art. The procedure is preferably carried out starting with the acid, for example in the presence of dicyclohexylcarbodiimide and dimethylaminopyridine or hydroxybenzotriazole, in an ether, for example tetrahydrofuran, a chlorinated solvent, for example dichloromethane, or dimethylformamide.

The reduction to an amine is likewise carried out, under the conventional conditions, for example by the action of a hydride such as lithium aluminum hydride, in an ether, for example tetrahydrofuran, or by the action of a borane in the presence of dimethyl sulfide.

When $R_4$ is a hydrogen atom, the condensation of the chain $R_3$ with the nitrogen of pyrrolidine or of azetidine does not require in principle that the nitrogen carrying $R_4$ is protected taking into account the steric hindrance around this nitrogen. Where appropriate, in the exceptional cases where this may prove necessary, a conventional group protecting the amine functional groups, such as those described in the book by T. W. Greene and P. G. M. Wuts cited above, may be used.

According to the invention, the preparation of the products of general formula (II) for which Y is a group $CH_2$ and m is equal to 1 or 2 is carried out by condensation of a heteroaromatic derivative of general formula (III):

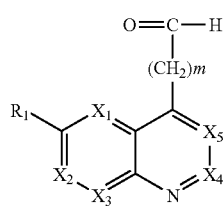

(III)

in which $R_1$, $X_1$, $X_2$, $X_3$, $X_4$ and $X_5$ are as defined above and m is equal to 1 or 2, with a derivative of general formula (IV):

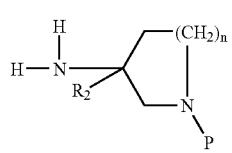

(IV)

in which P is a protecting group, n and $R_2$ are as defined above and $R_2$ represents a protected radical if $R_2$ represents or carries a carboxylic acid functional group, followed by the removal of the protecting groups and/or followed by the conversion, by a subsequent operation, of the substituents of the aromatic bicycle of general formula (II) thus obtained, to give the expected derivative carrying the radical $R_1$, $R'_1$, $R'_2$, $R'_3$, $R'_4$, $R'_5$, and where appropriate removal of the protecting radical(s) still present in the molecule.

P may be any group protecting the nitrogen atom, which is compatible with the reaction (t-butyloxycarbonyl, benzyloxycarbonyl for example). The groups protecting the acid functional groups are chosen from the customary groups whose introduction and removal do not affect the remainder of the molecule, in particular those mentioned in the references cited above.

The reaction may be carried out in the presence of an amine-containing base such as triethylamine, in a halogenated solvent such as chloroform or dichloroethane and then a reducing agent such as sodium triacetoxyborohydride in the presence of acetic acid, the procedure being carried out at room temperature.

In the case where m is equal to 0, the preparation is carried out under similar conditions, using at the start a derivative of general formula

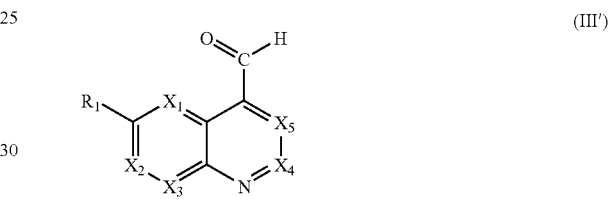

(III')

in which $R_1$, $X_1$, $X_2$, $X_3$, $X_4$ and $X_5$ are as defined above.

According to the invention, the products of general formula (II) for which Y is a CHR group, R being an alkyl, may be prepared starting with the corresponding compounds in which Y is $CH_2$, by the action of an alkyl halide, preferably an iodide on the anion at the α-position of the quinoline, prepared by the action of a strong base, for example an alkali metal tert-butoxide. Such reactions are known to persons skilled in the art.

According to the invention, the preparation of the products of general formula (II) for which Y is a CHOH group and m=1 is carried out by condensation of a derivative of general formula

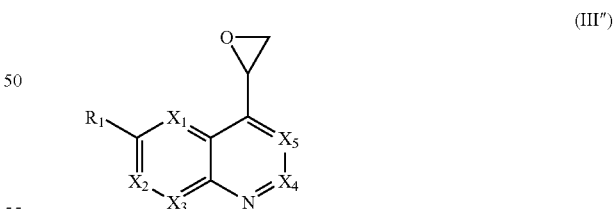

(III'')

in which $R_1$, $X_1$, $X_2$, $X_3$, $X_4$ and $X_5$ are as defined above, with a derivative of general formula IV) as defined above. The procedure may be carried out in the presence of lithium or sodium perchlorate in a solvent such as dimethylformamide, in the hot state.

The products of general formula (II) for which Y is a carbonyl group and m=1 or 2 may be prepared by oxidation of the corresponding derivative of general formula (II) for which Y is a CHOH group. This oxidation is carried out for example using potassium permanganate, optionally in a sodium hydroxide solution (for example 3 N sodium hydroxide), at a temperature of between −20 and 20° C., or alternatively by the action of oxalyl chloride in the presence of dimethyl sulfoxide, followed by the addition of an amine such as triethylamine, in an inert solvent such as dichloromethane, dimethyl sulfoxide at a temperature of between −60 and 20° C. by analogy with the method described by D. SWERN et al., J. Org. Chem., 44, 4148 (1979).

The products of general formula (II) for which Y is a carbonyl group and m=0 may be obtained by a peptide coupling reaction of the amine of formula (IV) with a product of general formula

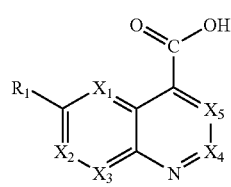

(III''')

in which $R_1$, $X_1$, $X_2$, $X_3$, $X_4$ and $X_5$ are as defined above.

The procedure is carried out for example in the presence of dicyclohexylcarbodiimide and 1-hydroxybenzotriazole.

The products of general formula (II) in which Y is a CROH group, R being an alkyl, may be obtained starting with products in which Y is a carbonyl group, by the reaction of an appropriate alkylmagnesium halide, under conventional conditions known to persons skilled in the art. The procedure is carried out for example by the action of methylmagnesium chloride in an ether such as tetrahydrofuran.

The products of general formula (II) in which Y is a CHR group, R being an alkyl, may also be obtained starting with products in which Y is a CROH group, which are obtained as described above, by removal of the alcohol by means of a xanthate. The alcohol is reacted with a strong base, for example sodium hydride, and then carbon disulfide is added, followed by methyl iodide. The xanthate thus obtained is then heated in the presence of tributyltin hydride.

The derivative of general formula (II) for which Y is a $CRNH_2$ group may be prepared from the corresponding CROH derivative which is converted to its tosylated derivative, with which ammonia is reacted. The procedure is carried out in an inert solvent such as N,N-dimethylformamide or dimethyl sulfoxide and preferably under pressure (2 to 20 atmospheres) at a temperature of between 20 and 100° C.

The tosyloxy derivative is obtained from the product of general formula (II) for which Y is CROH, by the action of tosyl chloride in pyridine, at a temperature between −10 and 20° C.

The derivatives of general formula (II) for which Y is a group CRF or $CF_2$ may be prepared by fluorination respectively from the derivative for which Y is a group CROH and that for which Y is a carbonyl group. The reaction is carried out in the presence of a sulfur fluoride [for example in the presence of aminosulfur trifluoride (diethylaminosulfur trifluoride (Tetrahedron, 44, 2875 (1988), bis(2-methoxyethyl)-aminosulfur trifluoride (Deoxofluor®), morpholinosulfur trifluoride for example) or alternatively in the presence of sulfur tetrafluoride (J. Org. Chem., 40, 3808 (1975)]. The fluorination reaction may also be carried out using a fluorinating agent such as hexafluoropropyl diethylamine (JP 2 039 546) or N-(2-chloro-1,1,2-trifluoroethyl) diethylamine.

The procedure is carried out in an organic solvent such as a chlorinated solvent (for example dichloromethane, dichloroethane, chloroform) or in an ether (tetrahydrofuran, dioxane for example) at a temperature of between −78 and 40° C. (preferably between 0 and 30° C.). It is advantageous to carry out the procedure in an inert medium.

The products of general formula (II) for which Y represents a CHOH group and m=1 or 2, may also be prepared by oxidation, in a basic medium, of the corresponding derivative for which Y is a group $CH_2$. The oxidation is carried out by the action of oxygen, preferably in an inert solvent such as dimethyl sulfoxide, in the presence of tert-butanol and of a base such as potassium or sodium tert-butoxide at a temperature of between 0 and 100° C.

The above reactions intended to occur at the level of Y on the product of formula (II) are performed, where appropriate, after protection of the reactive functional groups of the pyrrolidine or of the azetidine and of the chain at the level of $R_4$. The protecting groups used are in particular those mentioned above.

The products of general formula (III) in which m=1 prepared starting with the product of formula (V):

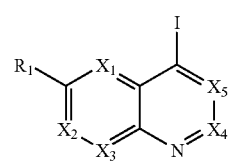

(V)

in which $R_1$, $X_1$, $X_2$, $X_3$, $X_4$ and $X_5$ are as defined above, which is reacted with allyltributyltin in the presence of tetrakistriphenylphosphinepalladium and copper iodide in dimethylformamide at 60° C., in order to obtain the allylated product of formula (VI):

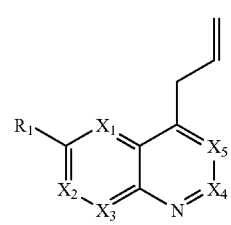

(VI)

which is oxidized with osmium tetroxide in the presence of N-methylmorpholine N-oxide, in a water-acetone mixture at room temperature, in order to obtain the diol of formula (VII):

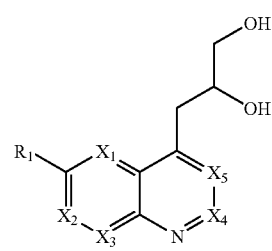

(VII)

which is oxidized with sodium periodate in a tetrahydrofuran-water mixture at room temperature.

The starting material of general formula (V) may be obtained as described in patent application WO 02/40474.

The product of general formula (III) in which m=2 may be prepared starting with a product of formula (VI) as defined above, which is subjected to a hydroboration reaction by treating with 9-borabicyclo[3.2.1]octane, followed by oxidation with hydrogen peroxide, in order to obtain the product of general formula (VIII):

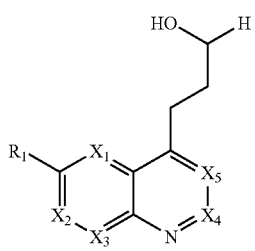

(VIII)

which is oxidized to the corresponding aldehyde of general formula (IX):

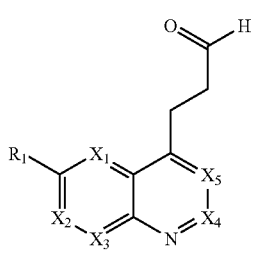

(IX)

for example by the so-called Swern method mentioned above. It is also possible to use the so-called Dess-Martin method, consisting in treating the alcohol under given conditions with periodinane (J.Org. Chem. 1983, p.48, 1.155-6).

The product of general formula (III') may be obtained starting with the product of general formula (X):

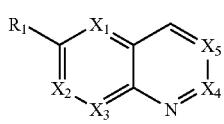

(X)

in which $R_1$, $X_1$, $X_2$, $X_3$, $X_4$ and $X_5$ are as defined above which is treated with a strong base, and then dimethylformamide is reacted with the anion thus obtained. The strong base is preferably butyllithium, sec-butyllithium or lithium diisopropylamide, and the procedure is carried out in a solvent such as for example ether or tetrahydrofuran, at a temperature between −78° C. and −40° C. The condensation of this lithium-containing derivative with DMF is carried out in the same solvent, at a temperature between −78° C. and 0° C.

The product of general formula (X) may be prepared according to a method described in patent application WO 02/40474.

The product of formula (III″) may be obtained starting with the product of general formula (X) as defined above, of which the anion at the 4-position is prepared as above, which is treated with acetaldehyde in order to obtain the alcohol of general formula (XI):

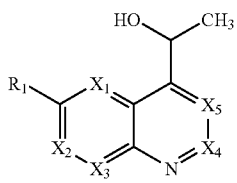

(XI)

which is oxidized to the corresponding ketone of formula (XII):

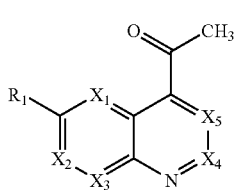

(XII)

which is treated with bromine in the presence of concentrated sulfuric acid, in order to obtain the product of general formula (XIII):

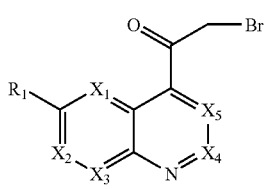

(XIII)

which is subjected to the action of an agent for reducing the ketone in order to obtain the product of general formula (XIV):

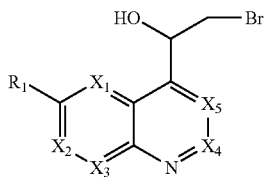

(XIV)

which is subjected to the action of a base in order to obtain the expected product.

The agent for reducing the ketone may be in particular boron hydride and the procedure is carried out for example in tetrahydrofuran. The base used is in particular an alkali metal carbonate or hydroxide and the procedure is carried out for example in an alkanol.

The product of general formula (III″) may be obtained starting with the product of general formula (X) as defined above, of which the anion at the 4-position is prepared, which is treated with an alkyl chloroformate, in order to obtain the ester of general formula (XV):

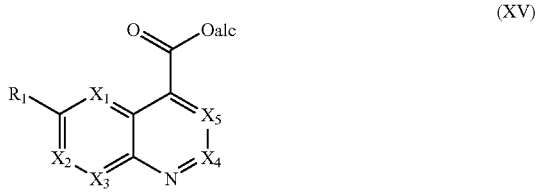

(XV)

which is saponified with a base under conventional conditions.

Products corresponding to the products of general formula (IV) as defined above, in which the reactive functional groups are free and some in which they are protected are described and, for some, commercially available, in the cases where n=0 or 1 and $R_2$=H, $CH_3$, $C_2H_5$, COOH, $COOCH_3$, $CH_2CO_2CH_3$, $CONH_2$, $CH_2OH$.

Among the literature references, there may be mentioned applications WO 9414794, WO 0170734, WO 9907696, EP 536035, EP 326916, EP 242789, JP 63130594 A2 and JP 62030776 A2, and the references Synlett (1991), 11, 783-4, Synthetic Comm. (1995), 25(9), 1295-1302, all of which are incorporated herein by reference in their entirety.

The products of formula (IV) which are not described may in general be obtained by methods described in these references or, starting with the products described, by methods known to persons skilled in the art.

According to the invention, products of general formula (I) for which $R_4$ is different from hydrogen may be obtained either as described above, starting with a product of general formula (II) for which $R_4$ has the corresponding value, different from hydrogen, or starting with a product of general formula (I) for which $R_4$ is hydrogen, by either of the methods described below.

According to the invention, the products of general formula (II) for which $R_4$ is different from hydrogen may be obtained starting with a product of general formula (II) for which $R_4$ is hydrogen, by the same methods.

Where appropriate, and in particular for the preparation of the products of general formula (II), the use of these methods requires the intermediate protection of the reactive functional groups, in particular the amino and/or carboxyl and/or hydroxyl functional groups.

This, and the deprotection, may be carried out according to the methods described above.

The products for which $R_4$ represents an alkyl radical may be obtained by the action of a corresponding aldehyde on the amine, in the presence of a reducing agent. This may be for example sodium borohydride or sodium cyanoborohydride or alternatively sodium triacetoxyborohydride and the procedure may be carried out in a conventional halogenated solvent or in an alcohol. It may be advantageous to carry out the procedure at a slightly acidic pH, for example in the presence of acetic acid.

The products for which $R_4$ represents a CHO radical may be obtained by the action of formic acid in the presence of acetic acid, or by the action of triethyl orthoformate in the presence of paratoluenesulfonic acid and triethylamine, on the amine. The procedure may be carried out in a halogenated solvent or in tetrahydrofuran or alternatively in dimethylformamide. It is also possible to carry out the formylation according to a Vilsmeyer type method.

The products for which $R_4$ represents a $COCH_3$ radical may be obtained by the action of an acetyl halide or acetic anhydride on the amine. The procedure is carried out in the presence of a base such as triethylamine.

The products for which $R_4$ represents a $CH_2CO_2H$ radical may be obtained by the action of bromoacetic acid on the amine, by carrying out the procedure under the same conditions as above, or by the action of glyoxaldehyde on the amine followed by reduction with sodium cyanoborohydride, by carrying out the procedure in the same type of solvents.

The products for which $R_4$ represents a CO—$CH_2$—$NH_2$ radical may be obtained by peptide coupling by the action of glycine on the amine, in the presence for example of dicyclohexylcarbodiimide, and after having protected the amine functional group of the glycine, or alternatively by the action on the amine of the same protected glycine, of which the acid functional group is activated beforehand, in particular in chloride form, by the action of oxalyl chloride or of thionyl chloride. The procedure is preferably carried out in a halogenated solvent or in tetrahydrofuran.

The intermediate products of general formula (II) for which the reactive functional groups are free or protected, obtained during the use of the method according to the invention are novel and, as such, form part of the invention.

Likewise, the intermediate products of general formulae (III), (III'), (III") and (III''') and their precursors of general formulae (VI), (VII), (VIII) and (IX), (XI), (XII), (XIII) and (XIV), and (XV) are also novel and, as such, also form part of the invention.

It is understood that the derivatives of general formula (I) and (II) can exist in enantiomeric or diastereoisomeric forms or in syn or anti form, which of course fall within the scope of the present invention. These forms may be separated according to the usual methods, known to persons skilled in the art, in particular by chiral chromatography or by High Performance Liquid Chromatography (HPLC). This is illustrated below in the experimental part.

The derivatives of general formula (I) can be purified, where appropriate, by physical methods such as crystallization or chromatography.

The derivatives of general formula (I) may be, where appropriate, converted to addition salts with acids or with bases by known methods. It is understood that these salts with acids or bases also fall within the scope of the present invention.

As examples of addition salts with pharmaceutically acceptable acids, there may be mentioned the salts formed with inorganic acids (for example hydrochlorides, hydrobromides, sulfates, nitrates or phosphates) or with organic acids (for example succinates, fumarates, tartrates, acetates, propionates, maleates, citrates, methanesulfonates, ethanesulfonates, phenylsufonates, p-toluenesulfonates, isethionates, naphthylsulfonates or camphorsulfonates) or with substitution derivatives of these acids.

The derivatives of general formula (I) carrying the carboxyl radical may be converted to metal salts or to addition salts with nitrogenous bases according to methods known per se. The salts may be obtained by the action of a metal (for example an alkali or alkaline-earth metal) base, of ammonia or of an amine, on a product according to the invention, in an appropriate solvent such as an alcohol, an ether or water, or by an exchange reaction with a salt of an organic acid. The salt formed precipitates after optional concentration of the solution, it is separated by filtration, decantation or lyophilization. As examples of pharmaceutically acceptable salts, there may be mentioned in particular the salts with alkali metals (sodium, potassium, lithium) or with alkaline earth metals (magnesium, calcium), ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, dibenzylamine).

The derivatives of general formula (I) according to the invention are particularly active antibacterial agents.

The study below demonstrates this.

a) Activity in vitro

The method of dilutions in agar medium in agreement with the NCCLS recommendations is used for the determination of the minimum inhibitory concentrations (MIC) expressed in µg/ml.

The activities of the compounds of Examples 1 to 4 are grouped together in the following table:

| Gram-positive MIC µg/ml at 24 hours | |
|---|---|
| S. aureus IP8203 sensitive | <0.06-4 |
| S. aureus AS 5155 methicillin resistant | <0.06-4 |
| S. pneumoniae 6254-01 $MLS_B$ resistant | <0.012-2 |
| E. faecalis ATCC29212 vancomycin resistant | 0.5-4 |
| Gram-negative MIC µg/ml at 48 hours | |
| M. catarrhalis IPA151 sensitive | <0.25-4 |
| H. influenzae 87169 sensitive | 4-32 |

In vitro, the compounds of the invention therefore proved quite remarkable both on Gram-positive microorganisms and on Gram-negative microorganisms.

b) The products according to the invention are particularly advantageous because of their low toxicity. None of the products exhibited toxicity at the dose of 50 mg/kg by the subcutaneous route or by the oral route in mice (2 administrations/day).

These properties make said products, and their salts with pharmaceutically acceptable acids and bases, suitable for use as medicaments in the treatment of conditions caused by sensitive microorganisms brought about by Gram-positive bacteria and in particular in those caused staphylococcus, such as staphylococcal septicemia, facial or cutaneous malignant staphylococcia, pyoderma, septic or suppurant wounds, anthrax, phlegmons, erysipela, primitive or post-influenza acute staphylococcia, bronchopneumonia, pulmonary suppurations, and in those caused by streptococci or enterococci.

These products may also be used as medicaments in the treatment of upper and lower respiratory infections caused by Gram-negative bacteria such as *Haemophilus influenzae* and *Moraxella catarrhalis*.

The subject of the present invention is therefore also, as medicaments and in particular medicaments intended for the treatment of bacterial infections in humans or animals, the compounds of general formula (I) as defined above and their pharmaceutically acceptable salts, in particular the preferred compounds mentioned above.

The present invention also relates to the pharmaceutical compositions containing at least one 4-substituted quinoline derivative according to the invention, where appropriate in salt form, in the pure state or in the form of a combination with one or more compatible and pharmaceutically acceptable diluents or adjuvants.

The compositions according to the invention may be used by the oral, parenteral, topical or rectal route or as aerosols.

As solid compositions for oral administration, there may be used tablets, pills, gelatin capsules, powders or granules. In these compositions, the active product according to the invention is mixed with one or more inert diluents or adjuvants, such as sucrose, lactose or starch. These compositions may comprise substances other than diluents, for example a lubricant such as magnesium stearate or a coating intended for a controlled release.

As liquid compositions for oral administration, there may be used solutions which are pharmaceutically acceptable, suspensions, emulsions, syrups and elixirs containing inert diluents such as water or paraffin oil. These compositions may also comprise substances other than diluents, for example wetting products, sweeteners or flavorings.

The compositions for parenteral administration may be sterile solutions or emulsions. As a solvent or vehicle, it is possible to use water, propylene glycol, a polyethylene glycol, vegetable oils, in particular olive oil, organic esters for injection, for example ethyl oleate. These compositions may also contain adjuvants, in particular wetting, isotonizing, emulsifying, dispersing and stabilizing agents.

The sterilization may be carried out in several ways, for example using a bacteriological filter, by irradiation or by heating. They may also be prepared in the form of sterile solid compositions which may be dissolved at the time of use in sterile water or any other sterile medium for injection.

The compositions for topical administration may be for example creams, ointments, lotions or aerosols.

The compositions for rectal administration are suppositories or rectal capsules which contain, in addition to the active ingredient, excipients such as cocoa butter, semisynthetic glycerides or polyethylene glycols.

The compositions may also be aerosols. For use in the form of liquid aerosols, the compositions may be stable sterile solutions or solid compositions dissolved at the time of use in pyrogen-free sterile water, in saline or any other pharmaceutically acceptable vehicle. For use in the form of dry aerosols intended to be directly inhaled, the active ingredient is finely divided and combined with a water-soluble solid diluent or vehicle having a particle size of 30 to 80 µm, for example dextran, mannitol or lactose.

In human therapy, the novel 4-substituted quinoline derivatives according to the invention are particularly useful in the treatment of infections of bacterial origin. The doses depend on the desired effects and the duration of the treatment. The doctor will determine the dosage which he judges most appropriate according to the treatment, according to the age, the weight, the degree of the infection and the other factors specific to the subject to be treated. Generally, the doses are between 750 mg and 3 g of active product in 2 or 3 doses per day by the oral route or between 400 mg and 1.2 g by the intravenous route for an adult.

The following examples illustrate compositions according to the invention.

a) A liquid composition intended for parenteral use is prepared according to the usual technique, comprising:

| | |
|---|---|
| 1-[(E)-3-(2,5-difluorophenyl)allyl]-3-[2-(3-fluoro-6-methoxy-4-quinolinyl)ethylamino]-3-pyrrolidinecarboxylic acid | 1 g |
| Glucose | qs 2.5% |
| Sodium hydroxide | qs pH = 4-4.5 |
| Water for injection | qs 20 ml | b) A liquid composition intended for parenteral use is prepared according to the usual technique, comprising:

| | |
|---|---|
| 1-[(E)-3-(2,5-difluorophenyl)allyl]-3-[2-(6-methoxy-4-quinolinyl)ethylamino]-3-pyrrolidinecarboylic acid; | [lacuna] |
| Glucose | qs 5% |
| Sodium hydroxide | qs pH = 4-4.5 |
| Water for injection | qs 50 ml |

The following examples illustrate the invention.

EXAMPLE 1

Enantiomers A and B of 1-[(E)-3-(2,5-difluorophenyl)-allyl]-3-[-2-(3-fluoro-6-methoxy-4-quinolinyl)-ethylamino]-3-pyrrolidinecarboxylic acid Enantiomer A of 1-[(E)-3-(2,5-difluorophenyl)allyl]-3-[-2-(3-fluoro-6-methoxy-4-quinolinyl)ethylamino]-3-pyrrolidinecarboxylic acid may be prepared in the following manner:

3.80 cm³ (19.00 mmol) of a 5 N aqueous sodium hydroxide solution are added, with stirring, to a solution containing 0.226 g (0.452 mmol) of the methyl ester of enantiomer A of 1-[(E)-3-(2,5-difluorophenyl)allyl]-3-[-2-(3-fluoro-6-methoxyquinolin-4-yl)ethylamino]-pyrrolidine-3-carboxylic acid in 25 cm³ of dioxane, and the yellow solution thus obtained is heated to reflux temperature and stirred for 18 hours at this temperature. The reaction medium is then brought to a temperature in the region of 20° C., and then concentrated to dryness under reduced pressure. The residue thus obtained is purified by chromatography on a column having a diameter of 2 cm, containing 15 cm of 20-45 µm silica at atmospheric pressure, using as eluent a chloroform/methanol/28% aqueous ammonia (12/3/0.5 by volume) mixture. The fractions containing the expected product are combined and concentrated under reduced pressure to give 0.150 g of a pale yellow product which is taken up in 20 cm³ of a dichloromethane/methanol (9/1) mixture. The resulting solution is filtered on paper, the paper is washed with twice 10 cm³ of a dichloromethane/methanol (9/1) mixture, the filtrates are combined and then concentrated to dryness under reduced pressure. The residue is taken up in 50 cm³ of isopropyl ether, and then the resulting suspension is concentrated to dryness under reduced pressure to give 0.138 g of the expected enantiomer A, in the form of a pale yellow amorphous solid.

$[\alpha]_D$=+25.5°+/−0.7 (c=0.5 in methanol) MS spectrum: CI m/z=486 MH⁺ base peak ¹H NMR spectrum (300 MHz, (CD₃)₂SO, δ in ppm): 1.82 (mt: 1H); 2.24 (mt: 1H); 2.40 (mt: 1H); 2.73 (d, J=11 Hz: 1H); from 2.75 to 3.05 (mt: 4H); from 3.05 to 3.40 (mt: 4H); 3.96 (s: 3H); 6.41 (dt, J=16 and 6 Hz: 1H); 6.58 (broad d, J=16 Hz: 1H); 7.13 (mt: 1H); 7.23 (split t, J=9.5 and 5 Hz: 1H); from 7.35 to 7.50 (mt: 1H); 7.38 (dd, J=9 and 3 Hz: 1H); 7.48 (d, J=3 Hz: 1H); 7.96 (d, J=9.5 Hz: 1H); 8.70 (broad s: 1H). IR spectrum (KBr pellet): 2962; 2834; 1621; 1512; 1490; 1385; 1264; 1240; 1145; 1033; 969; 825; 799 and 727 cm⁻¹

Enantiomer B of 1-[(E)-3-(2,5-difluorophenyl)allyl]-3-[-2-(3-fluoro-6-methoxy-4-quinolinyl)ethylamino]-3-pyrrolidinecarboxylic acid may be prepared in the following manner:

3.85 cm³ (19.24 mmol) of a 5 N aqueous sodium hydroxide solution are added, with stirring, to a solution containing 0.229 g (0.458 mmol) of the methyl ester of the enantiomer B of 1-[(E)-3-(2,5-difluorophenyl)-allyl]-3-[-2-(3-fluoro-6-methoxy-4-quinolinyl)ethyl-amino]-3-pyrrolidinecarboxylic acid in 25 cm³ of dioxane, and the yellow solution thus obtained is heated to the reflux temperature, and stirred for 18 hours at this temperature. The reaction medium is then brought to a temperature in the region of 20° C., and then concentrated to dryness under reduced pressure. The residue thus obtained is purified by chromatography on a column having a diameter of 2 cm, containing 21 cm of 20-45 µm silica at atmospheric pressure using as eluent a chloroform/methanol/28% aqueous ammonia (12/3/0.5 by volume) mixture. The fractions containing the expected product are combined and concentrated under reduced pressure to give 0.150 g of a pale yellow product which is taken up in 20 cm³ of a dichloromethane/methanol (9/1) mixture. The resulting solution is filtered on paper, the paper is washed with twice 10 cm³ of a dichloromethane/methanol (9/1) mixture, the filtrates are combined and then concentrated to dryness under reduced pressure. The residue is taken up in 50 cm³ of isopropyl ether, and then the resulting suspension is concentrated to dryness under reduced pressure to give 0.143 g of the expected enantiomer B in the form of a pale yellow amorphous solid.

$[\alpha]_D$=−21.60°+/−0.7 (c=0.5 in methanol) MS spectrum: CI m/z=486 MH⁺ base peak ¹H NMR spectrum (300 MHz, (CD₃)₂SO with addition of a few drops of CD₃COOD d4, δ in ppm): 2.02 (mt: 1H); 2.33 (mt: 1H); 2.65 (mt: 1H); 2.94 (d, J=11 Hz: 1H); from 3.00 to 3.20 (mt: 3H); 3.22 (d, J=11 Hz: 1H); from 3.30 to 3.50 (mt: 4H); 3.93 (s: 3H); 6.41 (dt, J=16 and 6 Hz: 1H); 6.67 (broad d, J=16 Hz: 1H); 7.14 (mt: 1H); 7.23 (split t, J=9.5 and 5 Hz: 1H); from 7.35 to 7.45 (mt: 1H); 7.38 (dd, J=9 and 3 Hz: 1H); 7.44 (d, J=3 Hz: 1H); 7.96 (d, J=9.5 Hz: 1H); 8.70 (broad s: 1H). IR spectrum (KBr pellet): 2928; 2835; 1621; 1510; 1490; 1384; 1264; 1239; 1146; 1032; 969; 825; 799 and 727 cm⁻¹

The enantiomers A and B of the methyl ester of 1-[(E)-3-(2,5-difluorophenyl)allyl]-3-[-2-(3-fluoro-6-methoxy-4-quinolinyl)ethylamino]-3-pyrrolidinecarboxylic acid may be prepared in the following manner:

2.3 g (16.5 mmol) of potassium carbonate, 0.603 g (3.63 mmol) of potassium iodide and, over 5 minutes, 30 cm³ of a solution containing 1 g (3.8 mmol) of (2,5-difluorophenyl) allyl chloride (prepared according to the method described in patent application WO 9307109) in anhydrous acetonitrile are added, with stirring and under an inert atmosphere, to a solution containing 1.15 g (3.3 mmol) of methyl ester of 3-(RS)-3-[-2-(3-fluoro-6-methoxy-4-quinolinyl)ethylamino]-3-pyrrolidinecarboxylic acid in 90 cm³ of anhydrous acetonitrile. The yellow suspension thus obtained is heated under reflux for 5 hours, and then brought to a temperature in the region of 20° C. and stirred for 18 hours. The reaction medium is then filtered, the residue is rinsed with 3 times 30 cm³ of acetonitrile and the filtrate is concentrated under reduced pressure. The residue thus obtained is taken up in 250 cm³ of ethyl acetate, the organic phase is washed with water, dried over anhydrous magnesium sulfate, filtered on paper and concentrated under reduced pressure. The orange oil thus obtained is purified by chromatography on a column having a diameter of 3.5 cm, containing 26 cm of 20-45 µm silica at atmospheric pressure using as eluent an ethyl acetate/methanol (90/10) mixture, followed by a dichloromethane/methanol (95/5) mixture. The fractions containing the expected product are combined and concentrated under reduced pressure to give 0.427 g of the methyl ester of 3-(RS)-1-[(E)-3-(2,5-difluoro-phenyl) allyl]-3-[-2-(3-fluoro-6-methoxyquinolin-4-yl)-ethylamino] pyrrolidin-3-carboxylic acid in the form of a viscous yellow oil.

MS spectrum: EI m/z=499 $M^+$; m/z=440 $(M-CO_2CH_3)^+$; m/z=346 $(M-C_9H_7F_2)^+$; m/z=279 $(M-C_{12}H_{13}ON_2F)^+$; m/z=153 $C_9H_7F_2^+$; m/z=42 $C_2H_4N^+$ base peak $^1H$ NMR spectrum (300 MHz, $(CD_3)_2SO$, δ in ppm): 1.70 (mt: 1H); 2.20 (mt: 1H); 2.40 (unresolved complex: 1H); from 2.55 to 2.80 (mt: 4H); 3.03 (broad d, J=10 Hz: 1H); from 3.10 to 3.20 (mt: 4H); 3.58 (s: 3H); 3.95 (s: 3H); 6.45 (dt, J=16 and 6 Hz: 1H); 6.58 (broad d, J=16 Hz: 1H); 7.13 (mt: 1H); 7.25 (split t, J=9.5 and 5 Hz: 1H); 7.39 (dd, J=9 and 3 Hz: 1H); 7.43 (d, J=3 Hz: 1H); 7.50 (ddd, J=9.5-6 and 3 Hz: 1H); 7.96 (d, J=9 Hz: 1H); 8.69 (broad s: 1H). IR spectrum (solution in $CH_2Cl_2$): 2985; 2805; 1730; 1621; 1508; 1490; 1469; 1277; 1232; 1145; 1088; 1030; 972 and 834 $cm^{-1}$ 0.294 g of 3-(RS)-1-[(E)-3-(2,5-difluorophenyl)allyl]-3-[2-(3-fluoro-6-methoxy-4-quinolinyl)ethylamino]-3-pyrrolidinecarboxylic acid methyl ester hydrochloride is also recovered in the form of a yellow oil.

MS spectrum: EI m/z=499 $M^+$; m/z=440 $(M-C_2CH_3)^+$; m/z=346 $(M-C_9H_7F_2)^+$; m/z=279 $(M-C_{12}H_{13}ON_2F)^+$; m/z=153 $C_9H_7F_2^+$; m/z=42 $C_2H_4N^+$ base peak The latter product is again put in its free base form by treating a solution in ethyl acetate containing it with an aqueous sodium bicarbonate solution, decanting the organic phase, drying over anhydrous magnesium sulfate and concentrating under reduced pressure. The product thus obtained is mixed with the preceding fraction, and then the two enantiomers are separated by chiral chromatography on Chiracel OD 20 μm phase, eluting with a Heptane 95% iPrOH 5% TEA 0.5% mixture. The detection is made at 265 nm. The following are thus obtained:

* 0.226 g of the enantiomer A of the methyl ester of 1-[(E)-3-(2,5-difluorophenyl)allyl]-3-[-2-(3-fluoro-6-methoxy-4-quinolinyl)ethylamino]-3-pyrrolidinecarboxylic acid in the form of an amber-colored gum.

$[α]_D$=+12.90°+/−0.7 (c=0.5 in methanol) MS spectrum: EI m/z=499 $M^+$; m/z=440 $(M-CO_2CH_3)^+$; m/z=346 $(M-C_9H_7F_2)^+$; m/z=279 $(M-C_{12}H_{13}ON_2F)^+$; m/z=153 $C_9H_7F_2^+$; m/z=42 $C_2H_4N^+$ base peak $^1H$ NMR spectrum (300 MHz, $(CD_3)_2SO$, δ in ppm): 1.70 (mt: 1H); 2.20 (mt: 1H); 2.39 (d, J=10 Hz: 1H); 2.48 (mt: 1H); from 2.55 to 2.80 (mt: 4H); 3.03 (d, J=10 Hz: 1H); 3.14 (broad d, J=6 Hz: 2H); 3.18 (broad t, J=7.5 Hz: 2H); 3.59 (s: 3H); 3.97 (s: 3H); 6.45 (dt, J=16 and 6 Hz: 1H); 6.59 (broad d, J=16 Hz: 1H); 7.13 (mt: 1H); 7.25 (split t, J=9.5 and 5 Hz: 1H); 7.39 (dd, J=9 and 3 Hz: 1H); 7.43 (d, J=3 Hz: 1H); 7.50 (ddd, J=9.5-6 and 3 Hz: 1H); 7.96 (d, J=9 Hz: 1H); 8.69 (broad s: 1H); IR spectrum (solution in $CCl_4$): 3077; 3033; 2935; 2928; 2832; 2801; 1732; 1622; 1507; 1490; 1469; 1431; 1263; 1232; 1217; 1140; 1034; 971; 909; 872 and 833 $cm^{-1}$

* and 0.229 g of the enantiomer B of the methyl ester of 1-[(E)-3-(2,5-difluorophenyl)allyl]-3-[-2-(3-fluoro-6-methoxy-4-quinolinyl)ethylamino]-3-pyrrolidinecarboxylic acid in the form of an amber-colored gum.

$[α]_D$=−5.2°+/−0.7 (c=0.5 in methanol) MS spectrum: EI m/z=499 $M^+$; m/z=440 $(M-CO_2CH_3)^+$; m/z=346 $(M-C_9H_7F_2)^+$; m/z=279 $(M-C_{12}H_{13}ON_2F)^+$; m/z=153 $C_9H_7F_2^+$; m/z=42 $C_2H_4N^+$ base peak $^1H$ NMR spectrum (300 MHz, $(CD_3)_2SO$, δ in ppm): 1.70 (mt: 1H); 2.20 (mt: 1H); 2.39 (d, J=10 Hz: 1H); 2.48 (t: J=7.5 Hz: 1H); from 2.55 to 2.80 (mt: 4H); 3.03 (d, J=10 Hz: 1H); 3.14 (broad d, J=6 Hz: 2H); 3.18 (broad t, J=7.5 Hz: 2H); 3.59 (s: 3H); 3.97 (s: 3H); 6.45 (dt, J=16 and 6 Hz: 1H); 6.59 (broad d, J=16 Hz: 1H); 7.13 (mt: 1H); 7.25 (split t, J=9.5 and 5 Hz: 1H); 7.39 (dd, J=9 and 3 Hz: 1H); 7.43 (d, J=3 Hz: 1H); 7.50 (ddd, J=9.5-6 and 3 Hz: 1H); 7.96 (d, J=9 Hz: 1H); 8.69 (broad s: 1H); IR spectrum (solution in $CCl_4$): 3077; 3033; 2935; 2928; 2831; 2800; 1733; 1622; 1507; 1490; 1469; 1431; 1263; 1232; 1217; 1140; 1034; 971; 909; 873 and 833 $cm^{-1}$ The methyl ester of 3-(RS)-3-[-2-(3-fluoro-6-methoxy-4-quinolinyl)ethylamino]-3-pyrrolidinecarboxylic acid may be prepared in the following manner:

25 $cm^3$ of cyclohexane are added, with stirring, to a solution containing 1.8 g (4.114 mmol) of the methyl ester of 3-(RS)-1-benzyl-3-[-2-(3-fluoro-6-methoxy-4-quinolinyl)ethylamino]-3-pyrrolidinecarboxylic acid in 160 $cm^3$ of methanol, followed by 1.8 g of 10% palladium on carbon.

The black suspension thus obtained is heated to reflux temperature and stirred for one hour at this temperature before being brought to a temperature in the region of 20° C. The reaction medium is filtered on paper and the residue is washed with 5 times 30 $cm^3$ of methanol. The filtrate is concentrated under reduced pressure to give 1.15 g of the expected ester in the form of a yellow oil.

MS spectrum: EI m/z=347 $M^+$; m/z=305 $(M-C_2H_4N)^+$; m/z=288 $(M-CO_2CH_3)^+$; m/z=192 $C_{11}H_{11}ONF^+$ base peak; m/z=157 $C_7H_{11}O_2N_2^+$; m/z=42 $C_2H_4N^+$ The methyl ester of 3-(RS)-1-benzyl-3-[-2-(3-fluoro-6-methoxy-4-quinolinyl)ethylamino]-3-pyrrolidinecarboxylic acid may be prepared in the following manner:

2.08 g (6.766 mmol) of 3-(RS)-3-amino-3-pyrrolidinecarboxylic acid methyl ester dihydrochloride (acid prepared according to the method described by Mamoun et al. *Synth. Commun.*, 1995, 25(9), 1295-1302) and, over 5 minutes, a solution containing 1.9 $cm^3$ (13.53 mmol) of triethylamine in solution in 30 $cm^3$ of anhydrous chloroform are added, with stirring and under an inert atmosphere (argon), to a suspension containing 1.5 g (6.766 mmol) of 3-(fluoro-6-methoxy-4-quinolinyl)-acetaldehyde in 70 $cm^3$ of anhydrous chloroform. The suspension is vigorously stirred under an inert atmosphere at a temperature in the region of 20° C. for 18 hours. The clear orange solution thus obtained is concentrated under reduced pressure to give a yellow residue which is taken up in 100 $cm^3$ of 1,2-dichloroethane and stirred at a temperature in the region of 20° C. 2.12 g (9.472 mmol) of sodium triacetoxyborohydride are added to the yellow suspension thus obtained, followed by 0.547 $cm^3$ (9.472 mmol) of acetic acid. The suspension thus obtained is stirred at a temperature in the region of 20° C. for 18 hours. The reaction medium is then diluted with 300 $cm^3$ of dichloromethane, the organic phase is washed with 5 times 150 $cm^3$ of water, dried over anhydrous magnesium sulfate, filtered on paper and then concentrated to dryness under reduced pressure. The residue thus obtained is purified by chromatography on 70-200 μm silica at atmospheric pressure using as eluent an ethyl acetate/methanol (95/5) mixture. The fractions containing the product are combined and concentrated under reduced pressure to give 1.8 g of the expected ester in the form of a yellow oil.

MS spectrum: EI m/z=437 $M^+$; m/z=378 $(M-CO_2CH_3)^+$; m/z=346 $(M-C_7H_7)^+$; m/z=219 $C_{13}H_{17}O_2N^+$; m/z=133 $C_9H_{11}N^+$; m/z=91 $C_7H_7^+$; m/z=42 $C_2H_4N^+$ base peak (3-Fluoro-6-methoxy-4-quinolinyl)acetaldehyde may be prepared in the following manner:

90 $cm^3$ of distilled water are added, with stirring, to a suspension containing 1.7 g (6.766 mmol) of 3-(3-fluoro-6-methoxy-4-quinolinyl)propane-1,2-diol in 90 $cm^3$ of tetrahydrofuran, followed by 7.3 g (33.83 mmol) of sodium periodate. The yellow suspension thus obtained is stirred for 90 minutes at a temperature in the region of 20° C., and then diluted with 300 cm³ of water. The aqueous phase is extracted with 3 times 200 cm³ of ethyl acetate, the organic phases are combined, washed with 3 times 100 cm³ of water. The emulsion thus created is taken up in 100 cm³ of brine, decanted, and the organic phases are dried over anhydrous magnesium sulfate, filtered on paper and then concentrated to dryness under reduced pressure to give 1.5 g of expected product, in the form of a pale yellow solid which is used as it is in the next step.

MS spectrum: EI m/z=219 M$^{+\cdot}$; m/z=191 (M-CO)$^{+\cdot}$ base peak 3-(3-Fluoro-6-methoxy-4-quinolinyl)propane-1,2-diol may be prepared in the following manner:

5.2 g (43.73 mmol) of N-methylmorpholine N-oxide are added, with stirring, to a solution containing 1.9 g (8.746 mmol) of 4-allyl-3-fluoro-6-methoxyquinoline in 75 cm³ of acetone and 15 cm³ of water, followed by 2 cm³ of a 2% solution of osmium tetroxide in tert-butyl alcohol. The black solution is stirred overnight at a temperature in the region of 20° C. The reaction medium is then cooled to a temperature in the region of 0° C., and then treated with 30 cm³ of a saturated aqueous $Na_2SO_3 \cdot 5H_2O$ solution. The solution thus obtained is stirred for 15 minutes at a temperature in the region of 0° C., and then diluted with 150 cm³ of ethyl acetate. The organic phase is decanted and the aqueous phase is extracted with 3 times 100 cm³ of ethyl acetate. The organic phases are combined, washed with 3 times 50 cm³ of water, and then dried over anhydrous magnesium sulfate, filtered on paper and concentrated to dryness under reduced pressure. The solid residue thus obtained is taken up in 50 cm³ of ethyl acetate and stirred for 30 minutes at a temperature in the region of 20° C. The suspension thus obtained is filtered, the solid is washed with ethyl acetate, and then with isopropyl ether. The solid thus obtained is dried in a desiccator under vacuum for 2 hours to give 1.6 g of expected product in the form of cream-colored crystals melting at 162° C.

MS spectrum: EI m/z=251 M$^{+\cdot}$; m/z=191 (M-$C_2H_4O_2$)$^{+\cdot}$ base peak; m/z=61 $C_2H_5O_2^+$ 4-Allyl-3-fluoro-6-methoxyquinoline may be prepared in the following manner:

7.2 cm³ (22.5 mmol) of allyltributyltin, 0.88 g (0.75 mmol) of tetrakis(triphenylphosphine)palladium and 0.575 g (3 mmol) of copper iodide (I) are added to a suspension containing 4.55 g (15 mmol) of 4-iodo-3-fluoro-6-methoxyquinoline (prepared according to the method described in patent application WO 0240474) in 150 cm³ of DMF. The suspension is stirred under an inert atmosphere (argon) and at a temperature in the region of 60° C. for 24 hours. The reaction medium is then brought to a temperature in the region of 20° C., diluted with 500 cm³ of ethyl acetate and washed with 3 times 300 cm³ of water. The emulsion which is formed is filtered on No. 4 sintered glass, and the residue is washed with 3 times 100 cm³ of water, and then with 3 times 100 cm³ of ethyl acetate. The organic phases are combined and dried over anhydrous magnesium sulfate. The suspension is filtered on paper, and the solution is concentrated to dryness under reduced pressure. The residue thus obtained is purified by chromatography on a 20-45 µm silica column at atmospheric pressure using as eluent a dichloromethane/ethyl acetate (95/5 by volume) mixture. The fractions containing the product are combined and concentrated under reduced pressure. 1.9 g of expected product are obtained in the form of a yellow oil.

MS spectrum: CI m/z=218 MH$^+$ base peak

EXAMPLE 2

Sodium salt of 3-(RS)-1-[(E)-3-(2,5-difluorophenyl)-allyl]-3-[-2-(3-chloro-6-methoxy-4-quinolinyl) ethyl-amino]-3-pyrrolidinecarboxylic acid 2.1 cm³ (10.18 mmol) of a 5 N aqueous sodium hydroxide solution are added, with stirring, to a solution containing 0.125 g (0.242 mmol) of the methyl ester of 3-(RS)-1-[(E)-3-(2,5-difluorophenyl)allyl]-3-[-2-(3-chloro-6-methoxy-4-quinolinyl)ethylamino]pyrrolidinecarboxylic acid in 20 cm³ of dioxane, and the orange solution thus obtained is heated to reflux temperature, and stirred for 18 hours at this temperature. The reaction medium is then brought to a temperature in the region of 20° C., and then concentrated to dryness under reduced pressure. The residue thus obtained is purified by chromatography on a column having a diameter of 2.5 cm, containing 15 cm of 20-45 µm silica at atmospheric pressure using as eluent a chloroform/methanol/28% aqueous ammonia (12/3/0.5) mixture. The fractions containing the expected product are combined and concentrated under reduced pressure. 0.038 g of the expected sodium salt is obtained in the form of a pale yellow foam.

Mass spectrum (EI): m/z=501 M$^{+\cdot}$; m/z=265 $C_{14}H_{13}O_2NF_2^+$; m/z=207 $C_{11}H_{10}ONCl^+$; m/z=153 $C_9H_7F_2^+$ (base peak); m/z=42 $C_2H_4N^{+1}H$ NMR spectrum (300 MHz, $(CD_3)_2SO$ with addition of a few drops of $CD_3COOD$ d4, δ in ppm): 2.05 (mt: 1H); 2.35 (mt: 1H); 2.72 (mt: 1H); 3.00 (broad d, J=10.5 Hz: 1H); 3.00 to 3.20 and 3.30 to 3.65 (mts: 7H); 3.25 (broad d, J=10.5 Hz: 1H); 3.97 (s: 3H); 6.42 (dt, J=16 and 7 Hz: 1H); 6.69 (broad d, J=16 Hz: 1H); from 7.05 to 7.30 (mt: 2H); from 7.35 to 7.45 (mt: 1H); 7.44 (broad dd, J=9 and 3 Hz: 1H); 7.50 (broad d, J=3 Hz: 1H); 7.97 (d, J=9 Hz: 1H); 8.68 (s: 1H). IR spectrum (KBr pellet): 3064; 2920; 2850; 2379; 1621; 1506; 1490; 1387; 1261; 1233; 1178; 1122; 1026; 971; 872; 825 and 727 cm$^{-1}$ The methyl ester of 3-(RS)-1-[(E)-3-(2,5-difluoro-phenyl)allyl]-3-[-2-(3-chloro-6-methoxy-4-quinolinyl)-ethylamino]-3-pyrrolidinecarboxylic acid may be prepared in the following manner:

0.456 g (3.3 mmol) of potassium carbonate, 0.121 g (0.726 mmol) of potassium iodide and, over 5 minutes, 10 cm³ of a solution containing 0.15 g (0.760 mmol) of (2,5-difluorophenyl)allyl chloride (prepared according to the method described in patent application WO 9307109) in anhydrous acetonitrile are added, with stirring and under an inert atmosphere (argon), to a solution containing 0.240 g (0.66 mmol) of methyl ester of 3-(RS)-3-[-2-(3-chloro-6-methoxy-4-quinolinyl)ethyl-amino]-3-pyrrolidinecarboxylic acid in 30 cm³ of anhydrous acetonitrile. The yellow suspension thus obtained is heated under reflux for 8 hours, and then brought to a temperature in the region of 20° C. and stirred for 18 hours. The reaction medium is then filtered, the residue is rinsed with 3 times 15 cm³ of acetonitrile and the filtrate is concentrated under reduced pressure. The residue thus obtained is taken up in 50 cm³ of ethyl acetate, the organic phase is washed with 3 times 15 cm³ of water, dried over anhydrous magnesium sulfate, filtered on paper and concentrated under reduced pressure. The orange oil thus obtained is purified by chromatography on a column having a diameter of 2 cm, containing 15 cm of 20-45 µm silica at atmospheric pressure using as eluent an ethyl acetate/methanol (95/5) mixture, and then an ethyl acetate/methanol (95/5) mixture. The fractions containing the product are combined and concentrated under reduced pressure. 0.147 g of expected product is obtained in the form of a yellow foam.

IR spectrum (KBr pellet): 2953; 2651; 1731; 1621; 1504; 1491; 1432; 1423; 1272; 1261; 1231; 1195; 1117; 1040; 1024; 973; 832 and 727 cm$^{-1}$ The methyl ester of 3-(RS)-3-[-2-(3-chloro-6-methoxy-quinolin-4-yl)ethylamino]pyrrolidine-3-carboxylic acid may be prepared in the following manner:

1.1 cm$^3$ (6.132 mmol, 3 equivalents) of a solution containing 33% of hydrobromic acid in acetic acid are added dropwise over about 15 minutes and at a temperature in the region of 15° C. to a solution containing 1.03 g (2.044 mmol) of the methyl ester of 1-vinyloxycarbonyl-3-{[2-(3-chloro-6-methoxy-4-quinolinyl)ethyl]vinyloxycarbonylamino}-3-pyrrolidinecarboxylic acid in 10 cm$^3$ of acetic acid under an inert atmosphere and with stirring. The orange solution thus obtained is stirred for 3 hours at a temperature in the region of 20° C. The reaction medium is then concentrated under reduced pressure, and the residue obtained is taken up in 50 cm$^3$ of water, the pH of the solution is brought to a value in the region of 9 with an aqueous NaHCO$_3$ solution, and the aqueous phase thus obtained is extracted with 3 times 100 cm$^3$ of ethyl acetate. The organic phases are combined, washed with 3 times 30 cm$^3$ of water, dried over anhydrous MgSO$_4$, filtered and concentrated under reduced pressure. The residue thus obtained is purified by chromatography on 20-45 µm silica at atmospheric pressure using as eluent a dichloromethane/methanol (50/50) mixture. The fractions containing the product are combined and concentrated under reduced pressure. 0.240 g of the expected ester is obtained in the form of an orange oil.

Mass spectrum (CI): m/z=364 MH$^+$ (peak base).

The methyl ester of 3-(RS)-1-vinyloxycarbonyl-3-{[2-(3-chloro-6-methoxy-4-quinolinyl)ethyl]vinyloxycarbonylamino}-3-pyrrolidinecarboxylic acid may be prepared in the following manner:

0.55 cm$^3$ (6.343 mmol, 2.2 equivalents) of vinyloxycarbonyl chloride is added to a solution containing 1.2 g (2.643 mmol) of the methyl ester of 3-(RS)-1-benzyl-3-[-2-(3-chloro-6-methoxy-4-quinolinyl)ethylamino]-3-pyrrolidinecarboxylic acid (prepared as below) in 100 cm$^3$ of 1,2-dichloroethane under an inert atmosphere and with stirring. The orange solution obtained is stirred for 1 hour at a temperature in the region of 20° C., and then for 3 hours at a temperature in the region of 100° C. The reaction medium is then concentrated under reduced pressure, and the residue thus obtained is purified by chromatography on 20-45 µm silica at atmospheric pressure using as eluent dichloromethane, and then a dichloromethane/ethyl acetate (95/5) mixture. The fractions containing the product are combined and concentrated under reduced pressure. 0.550 g of the expected ester are obtained in the form of an orange oil.

Mass spectrum (CI): m/z=504 MH$^+$ (base peak).

EXAMPLE 3

3-(RS)-1-[(E)-3-(2,5-Difluorophenyl)allyl]-3-[-2-(6-methoxy-4-quinolinyl)ethylamino]-3-pyrrolidinecarboxylic acid 7.7 cm$^3$ (38.39 mmol) of a 5 N aqueous sodium hydroxide solution are added, with stirring, to a solution containing 0.44 g (0.914 mmol) of the methyl ester of 3-(RS)-1-[(E)-3-(2,5-difluorophenyl)allyl]-3-[-2-(6-methoxy-4-quinolinyl)ethylamino]-3-pyrrolidinecarboxylic acid in 50 cm$^3$ of dioxane, and the orange solution thus obtained is heated to reflux temperature, and stirred for 18 hours at this temperature. The reaction medium is then brought to a temperature in the region of 20° C., and then concentrated to dryness under reduced pressure. The residue thus obtained is purified by chromatography on a column having a diameter of 2 cm, containing 21 cm of 20-45 µm silica at atmospheric pressure using as eluent a dichloromethane/methanol/28% aqueous ammonia (40/5/0.5) mixture. The fractions containing the expected product are combined and concentrated under reduced pressure to give 0.360 g of a pale yellow foam which is taken up in 25 cm$^3$ of a dichloromethane/methanol (9/1) mixture. The resulting solution is filtered, the filter is washed with a dichloromethane/methanol (9/1) mixture, the filtrates are combined and then concentrated to dryness under reduced pressure. The residue is taken up in 50 cm$^3$ of isopropyl ether, stirred for 10 minutes, and then the resulting suspension is concentrated to dryness under reduced pressure to give 0.330 g of the expected acid in the form of a pale yellow solid.

MS spectrum: EI m/z=467 M$^{+\cdot}$; m/z=282 (M-C$_{12}$H$_{11}$ON)$^+$; m/z=185 C$_{12}$H$_{11}$ON$^{+\cdot}$ base peak; m/z=42 C$_2$H$_4$N$^{+1}$H NMR spectrum (300 MHz, (CD$_3$)$_2$SO with addition of a few drops of CD$_3$COOD, δ in ppm): 2.05 (mt: 1H); 2.34 (mt: 1H); 2.65 (mt: 1H); 2.95 (d, J=11 Hz: 1H); from 3.05 to 3.20 (mt: 3H); 3.25 (d, J=11 Hz: 1H); from 3.30 to 3.50 (mt: 4H); 3.92 (s: 3H); 6.42 (dt, J=16 and 6 Hz: 1H); 6.7 (broad d, J=16 Hz: 1H); 7.13 (mt: 1H); 7.23 (split t, J=9.5 and 5 Hz: 1H); from 7.35 to 7.50 (mt: 4H); 7.95 (d, J=9.5 Hz: 1H); 8.66 (d, J=4.5 Hz: 1H). IR spectrum (KBr pellet): 2961; 2832; 1621; 1592; 1510; 1490; 1476; 1431; 1367; 1263; 1242; 1228; 1145; 1082; 1030; 969; 847; 821 and 727 cm$^{-1}$ The methyl ester of 3-(RS)-1-[(E)-3-(2,5-difluoro-phenyl)allyl]-3-[-2-(6-methoxy-4-quinolinyl)ethylamino]-3-pyrrolidinecarboxylic acid may be prepared in the following manner:

1.82 g (10.94 mmol) of potassium carbonate, 0.400 g (2.406 mmol) of potassium iodide and, over 5 minutes, 10 cm$^3$ of a solution containing 0.600 g (2.517 mmol) of (2,5-difluorophenyl)allyl chloride (prepared according to the method described in patent application WO 9307109) in anhydrous acetonitrile are added, with stirring and under an inert atmosphere (argon), to a solution containing 0.8 g (2.187 mmol) of 3-(RS)-3-[-2-(6-methoxy-4-quinolinyl)ethylamino]-3-pyrrolidinecarboxylic acid methyl ester dihydrochloride in 60 cm$^3$ of anhydrous acetonitrile. The yellow suspension thus obtained is heated under reflux for 5 hours, and then brought to a temperature in the region of 20° C. and stirred for 18 hours. The reaction medium is then filtered on No. 4 sintered glass, the residue is rinsed with 3 times 30 cm$^3$ of acetonitrile and the filtrate is concentrated under reduced pressure. The residue thus obtained is taken up in 250 cm$^3$ of ethyl acetate, the organic phase is washed with 3 times 100 cm$^3$ of water, dried over anhydrous magnesium sulfate, filtered and concentrated under reduced pressure. The orange oil thus obtained is purified by chromatography on 70-200 µm silica at atmospheric pressure using as eluent an ethyl acetate/methanol (90/10) mixture, and then a dichloromethane/methanol (90/10) mixture. The fractions containing the expected product are combined and concentrated under reduced pressure. 0.460 g of the expected ester is obtained in the form of a yellow oil.

MS spectrum: ES m/z=431 MH$^+$ base peak $^1$H NMR spectrum (300 MHz, (CD$_3$)2SO, δ in ppm): 1.27 (mt: 1H); 2.23 (mt: 1H); 2.46 (d, J=10 Hz: 1H); from 2.50 to 2.85 (mt: 5H); 3.05 (d, J=10 Hz: 1H); from 3.10 to 3.25 (mt: 4H); 3.60

(s: 3H); 3.95 (s: 3H); 6.47 (dt, J=16 and 6 Hz: 1H); 6.62 (broad d, J=16 Hz: 1H); 7.14 (mt: 1H); 7.26 (split t, J=9.5 and 5 Hz: 1H); 7.35 (d, J=4.5 Hz: 1H); 7.40 (mt: 2H); 7.51 (ddd, J=9.5-6 and 3 Hz: 1H); 7.94 (d, J=9 Hz: 1H); 8.64 (d, J=4.5 Hz: 1H). IR spectrum (solution in $CCl_4$): 3076; 3031; 2952;, 2907; 2833; 2800; 1733; 1621; 1593; 1508; 1490; 1474; 1431; 1262; 1241; 1229; 1196; 1036; 971; 872 and 850 $cm^{-1}$ 3-(RS)-3-[-2-(6-methoxy-4-quinolinyl)ethylamino]-3-pyrrolidinecarboxylic acid methyl ester dihydrochloride may be prepared in the following manner:

15 $cm^3$ of cyclohexene are added, with stirring, to a solution containing 1.2 g (2.643 mmol) of the methyl ester of 3-(RS)-1-benzyl-3-[-2-(3-chloro-6-methoxy-4-quinolinyl)ethylamino]-3-pyrrolidinecarboxylic acid in 100 $cm^3$ of methanol, followed by 1.2 g of 10% palladium on carbon. The black suspension thus obtained is heated under reflux and stirred for one hour at this temperature, before being brought to a temperature in the region of 20° C. The reaction medium is filtered and the residue is washed with 5 times 20 $cm^3$ of methanol. The filtrate is concentrated under reduced pressure to give 0.8 g of dihydrochloride of the expected ester in the form of a yellow oil.

MS spectrum: EI m/z=329 $M^{+\cdot}$; m/z=287 $(M-C_2H_4N)^{+\cdot}$; m/z=270 $(M-CO_2CH_3)^+$; m/z=173 $C_{11}H_{11}ON^{+\cdot}$ base peak; m/z=42 $C_2H_4N^+$; m/z=36 $HCl^{+\cdot}$ The methyl ester of 3-(RS)-1-benzyl-3-[-2-(3-chloro-6-methoxy-4-quinolinyl)ethylamino]-3-pyrrolidinecarboxylic acid may be prepared in the following manner:

1.38 g (4.5 mmol) of 3-(RS)-3-amino-3-pyrrolidinecarboxylic acid methyl ester dihydrochloride and, over 5 minutes, a solution containing 1.27 $cm^3$ (9 mmol) of triethylamine in solution in 15 $cm^3$ of anhydrous chloroform are added, with stirring and under an inert atmosphere (argon), to a suspension containing 1.06 g (4.5 mmol) of (3-chloro-6-methoxy-4-quinolinyl)-acetaldehyde in 45 $cm^3$ of anhydrous chloroform. The suspension is vigorously stirred under an inert atmosphere at a temperature in the region of 20° C. for 18 hours. The solution thus obtained is concentrated under reduced pressure to give a residue which is taken up in 60 $cm^3$ of 1,2-dichloroethane and stirred at a temperature in the region of 20° C. 1.4 g (6.3 mmol) of sodium triacetoxyborohydride are added to the suspension thus obtained, followed by 0.364 $cm^3$ (6.3 mmol) of acetic acid. The suspension thus obtained is stirred at a temperature in the region of 20° C. for 18 hours. The reaction medium is then diluted with 250 $cm^3$ of dichloromethane, the organic phase is washed with 5 times 100 $cm^3$ of water, dried over anhydrous magnesium sulfate, filtered and concentrated to dryness under reduced pressure. The residue thus obtained is purified by chromatography on 70-200 μm silica at atmospheric pressure using as eluent an ethyl acetate/methanol (95/5) mixture. The fractions containing the product are combined and concentrated under reduced pressure. 1.2 g of the expected methyl ester are obtained in the form of a yellow oil.

MS spectrum: EI m/z=453 $M^{+\cdot}$; m/z=394 $(M-CO_2CH_3)^+$; m/z=362 $(M-C_7H_7)^+$; m/z=219 $C_{13}H_{17}O_2N^{+\cdot}$; m/z=133 $C_9H_{11}N^{+\cdot}$; m/z=91 $C_7H_7^+$; m/z=42 $C_2H_4N^+$ base peak (3-Chloro-6-methoxy-4-quinolinyl)acetaldehyde may be prepared in the following manner:

60 $cm^3$ of distilled water are added, with stirring, to a suspension containing 1.2 g (4.55 mmol) of 3-(3-chloro-6-methoxy-4-quinolinyl)propane-1,2-diol in 60 $cm^3$ of tetrahydrofuran, followed by 4.8 g (22.5 mmol) of sodium periodate. The yellow suspension thus obtained is stirred for 90 minutes at a temperature in the region of 20° C., and then diluted with 280 $cm^3$ of water. The aqueous phase is extracted with 3 times 150 $cm^3$ of ethyl acetate, the organic phases are combined, washed with 3 times 100 $cm^3$ of water. The emulsion thus created is taken up in 100 $cm^3$ of brine, decanted, and the organic phases are dried over anhydrous magnesium sulfate, filtered on paper and then concentrated to dryness under reduced pressure to give 1.1 g of expected product in the form of a pale yellow solid which is used as it is in the next step.

MS spectrum: EI m/z=235 $M^{+\cdot}$; m/z=207 $(M-CO)^{+\cdot}$ base peak 3-(3-Chloro-6-methoxy-4-quinolin-4-yl)propane-1,2-diol may be prepared in the following manner:

4.7 g (39.58 mmol) of N-methylmorpholine N-oxide are added, with stirring, to a solution containing 1.85 g (7.916 mmol) of 4-allyl-3-chloro-6-methoxyquinoline in 75 $cm^3$ of acetone and 15 $cm^3$ of water, followed by 1.8 $cm^3$ of a solution containing 2% osmium tetroxide in tert-butyl alcohol. The black solution is stirred overnight at a temperature in the region of 20° C. The reaction medium is then cooled to a temperature in the region of 0° C., and then treated with 30 $cm^3$ of a saturated aqueous $Na_2SO_3.5H_2O$ solution. The solution thus obtained is stirred for 15 minutes at a temperature in the region of 0° C., and then diluted with 150 $cm^3$ of ethyl acetate. The organic phase is decanted and the aqueous phase is extracted with 3 times 100 $cm^3$ of ethyl acetate. The organic phases are combined, washed with 3 times 50 $cm^3$ of water, and then dried over anhydrous magnesium sulfate, filtered and concentrated to dryness under reduced pressure. The solid residue thus obtained is taken up in 50 $cm^3$ of ethyl acetate and stirred for 30 minutes at a temperature in the region of 20° C. The suspension thus obtained is filtered, the solid is washed with 3 times 10 $cm^3$ of ethyl acetate, and then with 3 times 10 $cm^3$ of isopropyl ether. The solid thus obtained is dried under reduced pressure for 2 hours. 1.2 g of expected product are obtained in the form of crystals melting at 138° C.

MS spectrum: EI m/z=267 $M^{+\cdot}$; m/z=207 $(M-C_2H_4O_2)^{+\cdot}$ base peak; m/z=61 $C_2H_5O_2^+$ 4-Allyl-3-chloro-6-methoxyquinoline may be prepared in the following manner:

14.4 $cm^3$ (45 mmol) of allyltributyltin, 1.75 g (1.5 mmol) of tetrakis(triphenylphosphine)palladium and 1.2 g (6 mmol) of copper iodide (I) are added to a suspension containing 8.2 g (30 mmol) of 4-bromo-3-chloro-6-methoxyquinoline (prepared according to the method described in patent application WO 0240474) in 250 $cm^3$ of DMF. The suspension is stirred under an inert atmosphere (argon) and at a temperature in the region of 60° C. for 48 hours. The reaction medium is then brought to a temperature in the region of 20° C., diluted with 500 $cm^3$ of ethyl acetate and washed with 3 times 300 $cm^3$ of water. The emulsion which is formed is filtered, and the residue is washed with 3 times 100 $cm^3$ of water, and then with 3 times 100 $cm^3$ of ethyl acetate. The organic phases are combined and dried over anhydrous magnesium sulfate. The medium is filtered and concentrated to dryness under reduced pressure. The residue thus obtained is purified by chromatography on a column having a diameter of 6 cm, containing 30 cm of 40-63 μm silica at atmospheric pressure using as eluent dichloromethane. The fractions containing the product are combined and 1.85 g of expected product are obtained in the form of an oil.

MS spectrum: IC m/z=234 $MH^+$ base peak

What is claimed is:

1. A compound of formula (I):

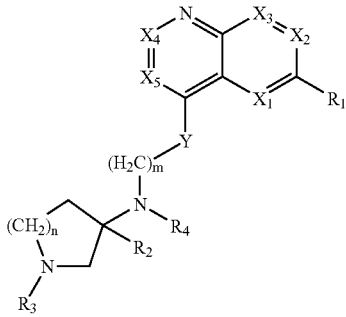

wherein:
X₁, X₂, X₃, X₄ and X₅ represent >C—R'₁ to >C—R'₅ respectively,

R₁, R'₁, R'₂, R'₃, R'₄ and R'₅ are identical or different and are independently selected from hydrogen, halogen, alkyl, cycloalkyl, phenyl, phenylthio, mono- or bicyclic heteroaryl or heteroarylthio, OH, SH, alkyloxy, difluoromethoxy, trifluoromethoxy, alkylthio, trifluoromethylthio, cycloalkyloxy, cycloalkylthio, acyl, acyloxy, acylthio, cyano, carboxyl, alkyloxycarbonyl, cycloalkyloxycarbonyl, nitro, —NRaRb or —CONRaRb radical, methylene radical substituted with fluoro, hydroxyl, alkyloxy, alkylthio, cycloalkyloxy, cycloalkylthio, phenyl, mono- or bicyclic heteroaryl, carboxyl, alkyloxycarbonyl, cycloalkyloxycarbonyl, —NRaRb or —CONRaRb, phenoxy, heterocyclyloxy, benzyloxy, heterocyclylmethyloxy, wherein Ra and Rb are identical or different and are independently selected from hydrogen, alkyl, cycloalkyl, phenyl, mono- or bicyclic heteroaryl; or Ra and Rb form together with the nitrogen atom to which they are attached a 5- or 6-membered heterocycle which may optionally contain another heteroatom chosen from O, S or N and optionally substituted with, where appropriate, alkyl, phenyl or mono- or bicyclic heteroaryl substituent on the nitrogen atom or, where appropriate, in which the sulfur atom is oxidized to the sulfinyl or sulfonyl state; or R₁ is difluoromethoxy, or a radical having the structure —$C_mF_{2m'+1}$, —$SC_mF_{2m'+1}$ or —$OC_mF_{2m'+1}$; wherein m' is an integer from 1 to 6; or R'₅ is trifluoroacetyl;
m is equal to 0, 1 or 2;
n is equal to 0 or 1;
Y is a divalent radical selected from CHR, C=O, when m is equal to 1 or 2, CROH, CRNH₂, CRF or CF₂; wherein
 R is hydrogen or (C₁₋₆)alkyl;
R₂ represents a radical R, —CO₂R, —CH₂CO₂R, —CH₂—CH₂CO₂R, —CONH₂, —CH₂—CONH₂, —CH₂—CH₂—CONH₂, —CH₂OH, —CH₂—CH₂OH, —CH₂—NH₂—CH₂—CH₂—NH₂ or —CH₂—CH₂—CH₂—NH₂;
wherein
 R is as defined above;
R₃ represents a radical phenyl, mono- or bicyclic heteroaryl, alk-R°₃, wherein alk is an alkylene radical and R°₃ represents hydrogen, halogen, hydroxyl, alkyloxy, alkylthio, alkylsulfinyl, alkylsulfonyl, alkylamino, dialkylamino, cycloalkyl, cycloalkyloxy, cycloalkylthio, cycloalylsulfinyl, cycloalkylsulfonyl, cycloalkylamino, N-cycloalkyl-N-alkylamino, —N-(cycloalkyl)₂, acyl, cycloalkylcarbonyl, phenyl, phenoxy, phenylthio, phenylsulfinyl, phenylsulfonyl, phenylamino, N-alkyl-N-phenylamino, N-cycloalkyl-N-phenylamino, —N-(phenyl)₂, phenylalkyloxy, phenylalkylthio, phenylalkylsulfinyl, phenylalkylsulfonyl, phenylalkylamino, N-alkyl-N-phenylaminoalkyl, N-cyclo-alkyl-N-phenylalkyl-amino, benzoyl, mono- or bicyclic heteroaryl, heteroaryloxy, heteroarylthio, heteroarylsulfinyl, heteroarylsulfonyl, heteroarylamino, N-alkyl-N-heteroarylamino, N-cycloalkyl-N-heteroarylamino, heteroarylcarbonyl, heteroarylalkyloxy, heteroarylalkylthio, heteroarylalkylsulfinyl, heteroarylalkylsulfonyl, heteroarylalkylamino, N-alkyl-N-heteroarylainoalkyl, N-cycloalkyl-N-heteroarylaminoalkyl, carboxyl, alkyloxycarbonyl, —NRaRb or —CO—NRakb wherein Ra and Rb respectively represent hydrogen, alkyl, cycloalkyl, phenyl, mono- or bicyclic heteroaryl, or one of Ra or Rb represents hydroxyl, alkyloxy, cycloalkyloxy, or Ra and Rb form together with the nitrogen atom to which they are attached a 5- or 6-membered heterocycle which optionally contain another heteroatom chosen from O, S and N and carrying, where appropriate, an alkyl, phenyl or mono- or bicyclic heteroaryl substituent on the nitrogen atom or where appropriate in which the sulfur atom is oxidized to the sulfinyl or sulfonyl state, or alternatively R°₃ represents —CR'b=CR'c-R'a for which R'a represents phenyl, phenylalkyl, heteroaryl or heteroarylaklyl in which the heteroaryl part is mono- or bicyclic, phenoxyalkyl, phenylthioalkyl, phenylsulfinylalkyl, phenylsulfonylalkyl, phenylaminoalkyl, N-alkyl-N-phenylaminoalkyl, heteroaryloxyalkyl, heteroarylthioalkyl, heteroarylsulfinylalkyl, heteroarylsulfonylalkyl, heteroarylaminoalkyl, N-alkyl-N-heteroarylaminoalkyl, heteroarylthio, heteroarylsulfinyl, heteroarylsulfonyl, phenylthio, phenylsulfinyl, phenylsulfonyl, and wherein R'b and R'c represent hydrogen, alkyl or cycloalkyl, or alternatively R°₃ represents a radical —C≡C—Rd for which Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, heteroarylaminoalkyl, N-alkyl-N-heteroarylaminoalkyl, (the heteroaryl parts mentioned above being mono- or bicyclic aromtaic), or alternatively R°₃ represents a radical —CF₂-phenyl or mono- or bicyclic —CF₂-heteroaryl, it being understood that the phenyl, benzyl, benzoyl or heteroaryl radicals or portions mentioned above are optionally substituted on the ring with 1 to 4 substituents chosen from halogen, hydroxyl, alkyl, alkyloxy, alkyloxyalkyl, haloalkyl, trifluoromethyl, trifluoromethoxy, trifluoromethylthio, carboxyl, alkyloxycarbonyl, cyano, alkylamino, —NRaRb for which Ra and Rb are as defined above, phenyl, hydroxyalkyl, alkylthioalkyl, alkylsulfinylalkyl, alkylsulfonylalkyl;

R₄ represents a radical R, —CHO, —COCH₃, —CH₂CO₂H or —COCH₂NH₂;

it being understood that the alkyl or acyl radicals and portions contain (unless otherwise stated) 1 to 10 carbon atoms in the form of a straight or branched chain and that the cycloalkyl radicals contain 3 to 6 carbon atoms; or its enantiomeric or diastereoisomeric forms or mixtures of these forms, and/or where appropriate in syn or anti form or mixtures thereof, and its salts.

2. The compound of formula (I) as set forth in claim 1, wherein:

$X_1$, $X_2$, $X_3$, $X_4$ and $X_5$ are as defined in claim 1;

$R_1$, $R'_1$, $R'_2$, $R'_3$, $R'_4$, $R'_5$ are identical or different and are independently selected from hydrogen, halogen, alkyl, alkyloxy, or methylene substituted with alkyloxy;

m is equal to 1;

n is equal to 1;

Y is a divalent radical selected from $CH_2$, CHOH, CHF, $CHNH_2$ or C=O;

$R_2$ is as defined in claim 1; and $R_3$ represents a radical alk-$R°_3$ for which alk is an alkylene radical and $R°_3$ represents alkyloxy, alkylthio, alkylamino, dialkylamino, cycloalkyloxy, cycloalkylthio, cycloalkylamino, N-cycloalkyl-N-alkylamino, —N-(cycloalkyl)$_2$, phenoxy, phenylthio, phenylamino, N-alkyl-N-phenylamino, N-cycloalkyl-N-phenylamino, phenylalkyloxy, phenylalkylthio, phenylalkylamino, N-alkyl-N-phenylaminoalkyl, N-cycloalkyl-N-phenylalkylamino, heteroaryl, oxy, heteroarylthio, heteroarylamino, N-alkyl-N-heteroarylamino, N-cycloalkyl-N-heteroarylamino, heteroarylcarbonyl, heteroarylalkyloxy, heteroarylalkylthio, heteroarylalkylamino, N-alkyl-N-heteroatylaminoalkyl, N-cycloalkyl-N-heteroarylaminoalkyl, (the heteroaryl parts cited above being mono- or bicyclic), —NRaRb or —CO—NRaRb wherein Ra and Rb are as defined in claim 1, or alternatively $R°_3$ represents —CR'b=CR'c-R'a for which R'a represents phenyl, phenylalkyl, heteroaryl or heteroarylalkyl, phenoxyalkyl, phenylthioalkyl, phenylamioalkyl, N-alkyl-N-phenylaminoalkyl, heteroaryloxyalkyl, heteroarylthioalkyl, heteroarylaminoalkyl, N-alkyl-N-heteroarylaminoalkyl, heteroarylthioalkyl, (the heteroaryl parts cited above being mono- or bicyclic), or phenylthio, and for which R'b and R'c represent hydrogen, alkyl or cycloalkyl, or alternatively $R°_3$ represents a radical —C≡C—Rd for which Rd is alkyl, phenyl, phenylalkyl, phenoxyalkyl, phenylthioalkyl, N-alkyl-N-phenylaminoalkyl, heteroaryl, heteroarylalkyl, heteroaryloxyalkyl, heteroarythioalkyl, heteroarylaminoalkyl, N-alkyl-N-heteroarylaminoalkyl, (the heteroaryl parts cited above being mono- or bicyclic), or alternatively $R°_3$ represents a radical —$CF_2$-phenyl or mono- or bicyclic —$CF_2$-heteroaryl;

$R_4$ is as defined in claim 1;

it being understood that the phenyl, benzyl, benzoyl or heteroaryl radicals or portions mentioned above may be optionally substituted as envisaged above; or its enantiomeric or diastereoisomeric forms or mixtures of these forms, and/or where appropriate in syn or anti form or mixtures thereof, and its salts.

3. The compound of formula (I) as set forth in claim 1, wherein:

$X_1$, $X_2$, $X_3$, $X_4$ and $X_5$ represent >C—$R'_1$ to >C—$R'_5$ respectively;

$R_1$, $R'_1$, $R'_2$, $R'_3$, $R'_4$ and $R'_5$ are identical or different and are independently selected from hydrogen, halogen, alkyl, alkyloxy or methylene substituted with alkyloxy;

m is equal to 1;

n is equal to 1;

Y is a divalent radical selected from $CH_2$, CHOH, CHF, $CHNH_2$ or C=O;

$R_2$ is as defined in claim 1;

$R_3$ represents a radical alk-$R°_3$ for which alk is an alkylene radical and $R°_3$ represents cycloalkyloxy, cycloalkylthio, phenoxy, phenylthio, phenylalkyloxy, phenylalkylthio, heteroaryl, oxy, heteroarylthio, heteroarylalkyloxy, heteroarylalkylthio, (the heteroaryl parts cited above being mono- or bicyolic) or alternatively $R°_3$ represents —CR'b=CR'c-R'a for which R'a represents phenyl, phenylthioalkyl, heteroaryl, heteroarylalkyl, phenoxyalkyl, phenylthioalkyl, heteroaryloxyalkyl, heteroarylthioalkyl, heteroarylthio (the heteroaryl parts cited above being mono- or bicyclic), or phenylthio, and for which R'b and R'c represent hydrogen, alkyl or cycloalkyl, or alternatively $R°_3$ represents a radical —C≡C—Rd for which Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroatylthioalkyl, (the heteroaryl parts cited above being mono- or bicyclic);

$R_4$ represents a radical R as defined in claim 1, it being understood that the phenyl, benzyl, benzoyl or heteroaryl radicals or portions mentioned above may be optionally substituted as envisaged above; or its enantiomeric or diastereoisomeric forms or mixtures of these forms, and/or where appropriate in syn or anti form or mixtures thereof, and its salts.

4. The compound of formula (I) as set forth in claim 1, which is selected from the following:

1-[(E)-3-(2,5-difluorophenyl)allyl]-3-[2-(3-fluoro-6-methoxyquinolin-4-yl)ethylamino]pyrrolidine-3-carboxylic acid;

1-[(E)-3-(2,5-difluorophenyl)allyl]-3-[2-(6-methoxyquinolin-4-yl)ethylamino]pyrrolidine-3-carboxylic acid;

methyl 1-[(E)-3-(2,5-difluorophenyl)ally]-3-[2-(3-fluoro-6-methoxyquinolin-4-yl)ethylamino]-pyrrolidine-3-carboxylate;

methyl 1-[(E)-3-(2,5-difluorophenyl)allyl]-3-[2-(6-methoxyquinolin-4-yl)ethylamino]pyrrolidine-3-carboxylate;

methyl 1-[(E)-3-(2,5-difuorophenyl)allyl]-3-[2-(3-chloro-6-methoxyquinolin-4yl)ethylainino]pyrrolidine-3-carboxylate;

methyl 1-[(E)-3-(2,5-difluorophenyl)allyl]-3-[2-(3-chloro-6-methoxyquinolin-4-yl)ethylamino]-pyrrolidine-3-carboxylate;

1-[(2E)-3-(2,5-difluorophenyl)-2-propenyl]-3-[[2-(3-fluoro-6-methoxy-4-quinolinyl)ethyl]methylamino]-3-pyrroldinecarboxylic acid;

1-[(2E)-3-(2,5-difluorophenyl)-2-propenyl]-3-[[2-(3-fluoro-6-methoxy-4-quinolinyl)ethyl]formylamino]-3-pyrrolidinecarboxylic acid;

3-[(aminoacetyl)[2-(3-fluoro-6-methoxy-4-quinolinyl)ethyl]amino]-1-[(2E)-3-(2,5-difluorophenyl)-2-propenyl]-3-pyrrolidinecarboxylic acid;

3-[(carboxymethyl)[2-(3-fluoro-6-methoxy-4-quinolinyl)ethyl]amino]-1-[(2E)-3-(2,5-difluorophenyl)-2-propenyl]-3-pyrrolidinecarboxylic adid;

N-[1-[(2E)-3-(2,5-difluorophenyl)-2-propenyl]-3-pyrrolidinyl]-3-fluoro-6-methoxy-4-quinolineethanamine;

N-[1-[(2E)-3-(2,5-difluorophenyl)-2-propenyl]-3-pyrrolidinyl]-N-[2-(3-fluoro-6-methoxy-4-quinolinyl)ethyl]glycine;

N-[1-[(2E)-3-(2,5-difluorophenyl)-2-propenyl]-3-pyrrolidinyl]-3-fluoro-6-methoxy-N-methyl-4-quinolineethanaiiine;

1-[(2E)-3-(2,5-difluorophenyl)-2-propenyl]-3-[[2-(3-fluoro-6-methoxy4-quinolinyl)ethyl]amino]-3-pyrrolidinemethanol;

1-[(2E)-3-(2,5-difluorophenyl)-2-propenyl]-3-[[2-(3-fluoro-6-methoxy-4-quinolinyl)ethyl]amino]-3-pyrrolidinecarboxamide;

N-[3-(aminomethyl)-1-[(2E)-3-(2,5-difluorophenyl)-2-propenyl]-3-pyrrolidinyl]-3-fluoro-6-methoxy-4-quinolineethanamine;

α[[[1-[(2E)-3-(2,5-difluorophenyl)-2-propenyl]-3-pyrrolidinyl]amino]methyl]-3-fluoro-6-methoxy-4-quinolinemethanol; or its enantiomeric or diastereoisomeric forms or mixtures of these forms, and/or where appropriate in syn or anti form or mixtures thereof, and its salts.

5. A method for the preparation of a compound of formula (I) as set forth in claim 1, comprising:

condensing a suitable compound having the radical $R_3$ with the 4-substituted quinoline derivative of formula (II):

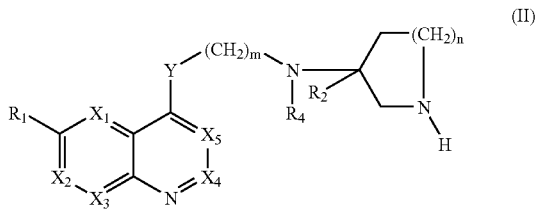

wherein $R_3$ is as defined in claim 1; and wherein $X_1$, $X_2$, $X_3$, $X_4$, $X_5$, $R_1$, $R_2$, Y, m and n are as defined in claim 1;

$R_2$ and $R_4$ being protected when they carry a carboxyl radical;

deprotecting, optionally, where appropriate, the group protecting the carboxyl radical; and, separating, optionally, where appropriate, the enantiomeric or diastereoisomeric forms or, where appropriate, the syn or anti forms; and converting, optionally, where appropriate, the product obtained into a salt.

6. The method as set forth in claim 5, wherein the condensation of the compound having the radical $R_3$ with the heterocyclic nitrogen is carried out by the action of a compound of formula (IIa):

wherein

X represents a halogen atom, a methylsulfonyl radical, a trifluoromethylsulfonyl radical or a p-toluenesulfonyl radical.

7. The method as set forth in claim 5, wherein when $R_3$ represents a radical -alk-$R_3$ wherein alk is an alkyl radical and $R_3$ represents a radical —C≡C—Rd, the reaction is carried out by condensation of an alkynyl halide H≡C-alk-X wherein alk is as defined above and X is a halogen atom, and then substitution of the chain with an appropriate radical Rd.

8. The method as set forth in claim 6, wherein when $R_3$ represents a radical -alk-$R_3$ wherein alk is an alkyl radical and $R_3$ represents a radical —C≡C—Rd, the reaction is carried out by condensation of an alkynyl halide HC≡C-alk-X wherein alk is as defined above and X is a halogen atom, and then substitution of the chain with an appropriate radical Rd.

9. The method as set forth in claim 5, wherein when $R_3$ represents a radical -alk-$R_3$ wherein alk is an alkyl radical and $R_3$ represents a phenoxy, phenylthio, phenylamino, heteroaryloxy, heteroarylthio or heteroarylamino radical, the reaction is carried out by first condensing a chain HO-alk-X for which X is a halogen atom, and then either converting the hydroxyalkyl chain obtained to a haloalkyl, methanesulfonylalkyl or p-toluenesulfonylalkyl chain and finally by causing an aromatic derivative having the structure $R_3H$ or $R_3H_2$ to act in a basic medium, or by causing the aromatic derivative to act directly under dehydration conditions.

10. The method as set forth in claim 6, wherein when R3 represents a radical -alk-$R°_3$ wherein alk is an alkyl radical and $R°_3$ represents a phenoxy, phenylthio, phenylamino, heteroaryloxy, heteroarylthio or heteroarylamino radical, the reaction is carried out by first condensing a chain HO-alk-X for which X is a halogen atom, and then either converting the hydroxyalkyl chain obtained to a haloalkyl, methanesulfonylalkyl or p-toluenesulfonylalkyl chain and finally by causing an aromatic derivative having the structure $R_3H$ or $R_3H_2$ to act in a basic medium, or by causing the aromatic derivative to act directly under dehydration conditions.

11. The method as set forth in claim 5, wherein the derivatives of formula (II) for which Y is a group $CH_2$ and m is equal to 1 or 2 are prepared by condensation of a heteroaromatic derivative of formula (III):

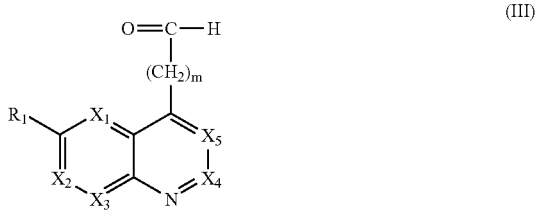

wherein $R_1$, $X_1$, $X_2$, $X_3$, $X_4$ and $X_5$ are as defined in claim 5 and m is equal to 1 or 2, with a derivative of general formula (IV):

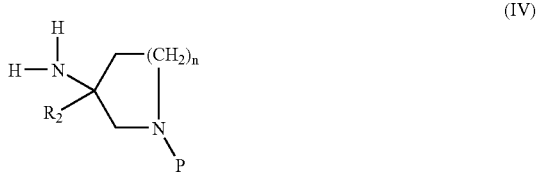

wherein P is a protecting group, and $R_2$ represents a protected radical if $R_2$ represents or carries a carboxylic acid functional group, followed by the removal of the protecting groups and/or followed by the conversion, by a subsequent operation, of the substituents of the aromatic bicycle of general formula (II) thus obtained, to give the expected derivative carrying the radical $R_1$, $R'_1$, $R'_2$, $R'_3$, $R'_4$, $R'_5$, and where appropriate removal of the protecting radical(s) still present in the molecule.

12. A compound of formula (II):

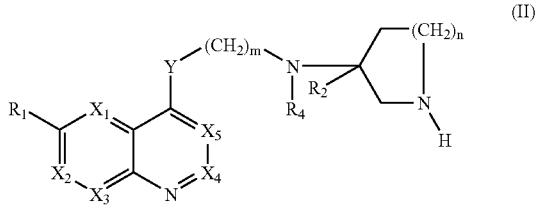

wherein $X_1$, $X_2$, $X_3$, $X_4$ and $X_5$ represent >C—$R'_1$, to >C—$R'_5$ respectively, alternatively at most one of them represents a nitrogen atom, $R_1$, $R'_1$, $R'_2$, $R'_3$, $R'_4$ and $R'_5$ are identical or different and are independendly selected from hydrogen, halogen, alkyl, cycloalkyl, phenyl, phenylthio, mono- or bicyclic heteroaryl or heteroarylthio, OH, SH, alkyloxy, difluoromethoxy, trifluoromethoxy, alkylthio, trifluoromethylthio, cycloalkyloxy, cycloalkylthio, acyl, acyloxy, acylthio, cyano, carboxyl, alkyloxycarbonyl, cycloalkyloxycarbonyl, nitro, —NRaRb or —CONRaRb radical, methylene radical substituted with fluoro, hydroxyl, alkyloxy, alkylthio, cycloalkyloxy, cycloalkylthio, phenyl, mono- or bicyclic heteroaryl, carboxyl, alkyloxycarbonyl, cycloalkyloxycarbonyl, —NRaRb or —CONRaRb, phenoxy, heterocyclyloxy, benzyloxy, heterocyclylmethyloxy, wherein Ra and Rb am identical or different and are independently selected from hydrogen, alkyl, cycloalkyl, phenyl, mono- or bicyclic heteroaryl; or Ra and Rb form together with the nitrogen atom to which they are attached a 5- or 6-membered heterocycle which may optionally contain another heteroatom chosen from O, S or N and optionally substituted with, where appropriate, alkyl, phenyl or mono- or bicyclic heteroaryl substituent on the nitrogen atom or, where appropriate, in which the sulfur atom is oxidized to the sulfinyl or sulfonyl state; or $R_1$ is difluoromethoxy, or a radical having the structure —$C_mF_{2m'+1}$, —$SC_mF_{2m'+1}$ or —$OC_mF_{2m'+1}$; wherein m' is an integer from 1 to 6; or $R_5$ is trifluoroacetyl;

m is equal to 0, 1 or 2;

n is equal to 0 or 1;

Y is a divalent radical selected from CHR, C=O or, when m is equal to 1 or 2, CROH, CRNH$_2$, CRF or CF$_2$; wherein R is hydrogen or ($C_{1-6}$)alkyl;

$R_2$ represents a radical R, —CO$_2$R, —CH$_2$CO$_2$R, —CH$_2$—CH$_2$CO$_2$R, —CONH$_2$, —CH$_2$—CONH$_2$, —CH$_2$—CH$_2$—CONH$_2$, —CH$_2$OH, —CH$_2$CH$_2$OH, —CH$_2$—NH$_2$—CH$_2$—CH$_2$—NH$_2$ or —CH$_2$—CH$_2$—CH$_2$—NH$_2$; wherein R is as defined above;

$R_4$ represents a radical R, —CHO, —COCH$_3$, —CH$_2$CO$_2$H or —COCH$_2$NH$_2$;

it being understood that the allyl or acyl radicals and portions contain (unless otherwise stated) 1 to 10 carbon atoms in the form of a straight or branched chain and that the cycloalkyl radicals contain 3 to 6 carbon atoms; or its enantiomeric or diastereolsomeric forms or mixtures of these forms, and/or where appropriate in syn or anti form or mixtures thereof, and its salts.

13. A phanaceutical composition comprising one or more compounds of formula (I) as set forth in claim 1 in combination with a pharmaceutically acceptable carrier.

14. A pharmaceutical composition comprising one or more compounds of formula (I) as set forth in claim 2 in combinion with a pharmaceutically acceptable carrier.

15. A pharmaceutical composition comprising one or more compounds of formula (I) as set forth in claim 3 in combination with a pharmaceutically acceptable carrier.

16. A pharmaceutical composition comprising one or more compounds of formula (I) as set forth in claim 4 in combination with a pharmaceutically acceptable carrier.

17. A pharmaceutical composition comprising at least one compound of formula (I) in the pure state and in combination with one or more compatible and pharmaceutically acceptable diluents and adjuvants:

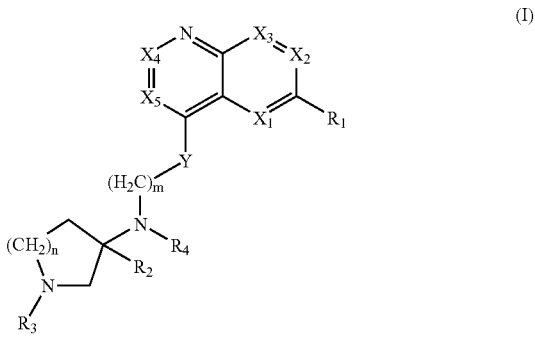

wherein:

$X_1$, $X_2$, $X_3$, $X_4$ and $X_5$ represent >C-$R'_1$ to >C-$R'_5$ respectively, $R_1$, $R'_1$, $R'_2$, $R'_3$, $R'_4$ and $R'_5$ are identical or different and are independently selected from hydrogen, halogen, alkyl, cycloalkyl, phenyl, phenylthio, mono- or bicyclic heteroaryl or heteroarylthio, OH, SH, alkyloxy, difluoromethoxy, trifluoromethoxy, alkylthio, trifluoromethylthio, cycloalkyloxy, cycloalkylthio, acyl, acyloxy, acylthio, cyano, carboxyl, alkyloxycarbonyl, cycloalkyloxycarbonyl, nitro, —NRaRb or —CONRaRb radical, methylene radical substituted with fluoro, hydroxyl, alkyloxy, alkylthio, cycloalkyloxy, cycloalkylthio, phenyl, mono- or bicyclic heteroaryl, carboxyl, alkyloxycarbonyl, cycloalkyloxycarbonyl, —NRaRb or —CONRaRb, phenoxy, heterocyclyloxy, benzyloxy, heterocyclylmethyloxy, wherein Ra and Rb are identical or different and are independently selected from hydrogen, alkyl, cycloalkyl, phenyl, mono- or bicyclic heteroaryl; or Ra and Rb form together with the nitrogen atom to which they are attached a 5- or 6-membered heterocycle which may optionally contain another heteroatom chosen from O, S or N and optionally substituted with, where appropriate, alkyl, phenyl or mono- or bicyclic heteroaryl substituent on the nitrogen atom or, where appropriate, in which the sulfur atom is oxidized to the sulfinyl or sulfonyl state; or $R_1$ is difluoromethoxy, or a radical having the structure —$C_mF_{2m'+1}$, —$SC_{m'}$, $F_{2m'+1}$ or —$OC_mF_{2m'+1}$; wherein m' is an integer from 1 to 6; or $R'_5$ is trifluoroacetyl;

m is equal to 0,1 or2;

n is equal to 0 or 1;

Y is a divalent radical selected from CHR, C=O or, when m is equal to 1 or 2, CROH, CRNH$_2$, CRF or CF$_2$;

wherein

R is hydrogen or (C$_{1-6}$) alkyl;

R$_2$ represents a radical R, —CO$_2$R, —CH$_2$CO$_2$R, —CH$_2$—CH$_2$CO$_2$R, —CONH$_2$, —CH$_2$—CONH$_2$, —CH$_2$—CH$_2$—CONH$_2$, —CH$_2$OH, —CH$_2$—CH$_2$OH, —CH$_2$—NH$_2$—CH$_2$—CH$_2$—NH$_2$ or —CH$_2$—CH$_2$—CH$_2$—NH$_2$;

wherein

R is as defined above;

R$_3$ represents a radical phenyl, mono- or bicyclic heteroaryl, alk—R$^o{}_3$, wherein alk is an alkylene radical and R$^o{}_3$ represents hydrogen, halogen, hydroxyl, alkyloxy, alkylthio, alkylsulfinyl, alkylsulfonyl, alkylamino, dialkylamino, cycloalkyl, cycloalkyloxy, cycloalkylthio, cycloalkylsulfinyl, cycloalkylsulfonyl, cycloalkylamino, N-cycloalkyl-N-alkylamino, —N-(cycloalkyl)$_2$, acyl, cycloalkylcarbonyl, phenyl, phenoxy, phenylthio, phenylsulfinyl, phenylsulfonyl, phenylamino, N-alkyl-N-phenylamino, N-cycloalkyl-N-phenylamino, —N-(phenyl)$_2$, phenylalkyloxy, phenylalkylthio, phenylalkylsulfinyl, phenylalkylsulfonyl, phenylalkylamino, N-alkyl-N-phenylaminoalkyl, N-cyclo-alkyl-N-phenylalkyl-amino, benzoyl, mono- or bicyclic heteroaryl, heteroaryloxy, heteroarylthio, heteroarylsulfinyl, heteroarylsulfonyl, heteroarylamino, N-alkyl-N-heteroarylamino, N-cycloalkyl-N-heteroarylamino, heteroarylcarbonyl, heteroarylalkyloxy, heteroarylalkylthio, heteroarylalkylsulfinyl, heteroarylalkylsulfonyl, heteroarylalkylamino, N-alkyl-N-heteroarylaminoalkyl, N-cycloalkyl-N-heteroarylaminoalkyl, carboxyl, alkyloxycarbonyl, —NRaRb or —CO-NRaRb wherein Ra and Rb respectively represent hydrogen, alkyl, cycloalkyl, phenyl, mono- or bicyclic heteroaryl, or one of Ra or Rb represents hydroxyl, alkyloxy, cycloalkyloxy, or Ra and Rb form together with the nitrogen atom to which they are attached a 5- or 6-membered heterocycle which optionally contain another heteroatom chosen from O, S and N and carrying, where appropriate, an alkyl, phenyl or mono- or bicyclic heteroaryl substituent on the nitrogen atom or where appropriate in which the sulfur atom is oxidized to the sulfinyl or sulfonyl state, or alternatively R$^o{}_3$ represents —CR'b=CR'c—R' a for which R'a represents phenyl, phenylalkyl, heteroaryl or heteroarylalkyl in which the heteroaryl part is mono- or bicyclic, phenoxyalkyl, phenylthioalkyl, phenylsulfinylalkyl, phenylsulfonylalkyl, phenylaminoalkyl, N-alkyl-N-phenylaminoalkyl, heteroaryloxyalkyl, heteroarylthioalkyl, heteroarylsulfinylalkyl, heteroarylsulfonylalkyl, heteroarylaminoalkyl, N-alkyl-N-heteroarylaminoalkyl, heteroarylthio, heteroarylsulfinyl, heteroarylsulfonyl, phenylthio, phenylsulfinyl, phenylsulfonyl, and wherein R'b and R'c represent hydrogen, alkyl or cycloalkyl, or alternatively R$^o{}_3$ represents a radical —C≡C—Rd for which Rd is alkyl, phenyl, phenylalkyl, phenoxyalkyl, phenylthioalkyl, N-alkyl-N-phenylaminoalkyl, mono- or bicyclic heteroaryl, heteroarylalkyl, heteroaryloxyalkyl, heteroarylthioalkyl, heteroarylaminoalkyl, N-alkyl-N-heteroarylaminoalkyl, (the heteroaryl parts mentioned above being mono- or bicyclic aromatic), or alternatively R$^o{}_3$ represents a radical —OF$_2$-phenyl or mono- or bicyclic —CF$_2$-heteroaryl, it being understood that the phenyl, benzyl, benzoyl or heteroaryl radicals or portions mentioned above are optionally substituted on the ring with 1 to 4 substituents chosen from halogen, hydroxyl, alkyl, alkyloxy, alkyloxyalkyl, haloalkyl, trifluoromethyl, trifluoromethoxy, trifluoromethylthio, carboxyl, alkyloxycarbonyl, cyano, alkylamino, —NRaRb for which Ra and Rb are as defined above, phenyl, hydroxyalkyl, alkyithioalkyl, alkylsulfinylalkyl, alkylsulfonylalkyl;

R$_4$ represents a radical R, —CHO, —COCH$_3$, —CH$_2$CO$_2$H or —COCH$_2$NH$_2$;

it being understood that the alkyl or acyl radicals and portions contain (unless otherwise stated) 1 to 10 carbon atoms in the form of a straight or branched chain and that the cycloalkyl radicals contain 3 to 6 carbon atoms; or its enantiomeric or diastereoisomeric forms or mixtures of these forms, and/or where appropriate in syn or anti form or mixtures thereof, and its salts.

\* \* \* \* \*